(12) United States Patent
Klee

(10) Patent No.: US 10,737,096 B1
(45) Date of Patent: Aug. 11, 2020

(54) CHARGE-BASED METHODS FOR MODIFYING NEURAL ACTIVITY

(71) Applicant: Maurice M. Klee, Fairfield, CT (US)

(72) Inventor: Maurice M. Klee, Fairfield, CT (US)

(*) Notice: Subject to any disclaimer, the term of this patent is extended or adjusted under 35 U.S.C. 154(b) by 0 days.

(21) Appl. No.: 15/728,585

(22) Filed: Oct. 10, 2017

Related U.S. Application Data

(60) Provisional application No. 62/412,328, filed on Oct. 25, 2016.

(51) Int. Cl.
*A61N 1/36* (2006.01)
*A61N 1/04* (2006.01)
*A61N 1/05* (2006.01)
*A61N 1/20* (2006.01)

(52) U.S. Cl.
CPC ......... *A61N 1/3615* (2013.01); *A61N 1/0456* (2013.01); *A61N 1/0551* (2013.01); *A61N 1/20* (2013.01); *A61N 1/36014* (2013.01); *A61N 1/36062* (2017.08); *A61N 1/36071* (2013.01); *A61N 1/36103* (2013.01); *A61N 1/0529* (2013.01); *A61N 1/36082* (2013.01)

(58) Field of Classification Search
CPC .............. A61N 1/3615; A61N 1/36062; A61N 1/0456; A61N 1/0551; A61N 1/36014; A61N 1/36071; A61N 1/36103; A61N 1/20; A61N 1/0529; A61N 1/36082
See application file for complete search history.

(56) References Cited

U.S. PATENT DOCUMENTS

| | | | |
|---|---|---|---|
| 7,340,299 B2 | 3/2008 | Puskas | |
| 7,346,382 B2 | 3/2008 | McIntyre et al. | |
| 7,684,866 B2 | 3/2010 | Fowler et al. | |
| 8,180,601 B2 | 5/2012 | Butson et al. | |
| 8,180,617 B1 | 5/2012 | Klee | |
| 8,494,627 B2 | 7/2013 | Bikson et al. | |
| 8,538,543 B2 | 9/2013 | McIntyre et al. | |

(Continued)

OTHER PUBLICATIONS

Baumann et al., "The Electrical Conductivity of Human Cerebrospinal Fluid at Body Temperature," IEEE Trans Biomed Eng. Mar. 1997;44(3):220-3.

(Continued)

*Primary Examiner* — William J Levicky
*Assistant Examiner* — Minh Duc G Pham

(57) ABSTRACT

This disclosure relates to methods for modifying neural activity by applying electrical current to a neural tissue, e.g., in a transcranial DC stimulation procedure (tDCS), a transcranial AC stimulation procedure (tACS), a transcranial random noise stimulation procedure (tRNS), a deep brain stimulation procedure (DBS), a transcutaneous electrical nerve stimulation procedure (TENS), or the like. Historically, computed potential, electrical field, and/or current density distributions have been used to select the locations of the electrodes that apply the electrical current. In the present disclosure, a computed charge distribution on the bounding surface of one or more sulci filled with cerebrospinal fluid (CSF) is used in selecting the electrode locations. In one embodiment, the sulcus's bounding surface is divided into pixels and each pixel's charge is determined by the pixel functioning as a sensor for the charges surrounding it, including the charges of other pixels and the charges on the electrodes.

17 Claims, 26 Drawing Sheets

(56) References Cited

U.S. PATENT DOCUMENTS

| | | | |
|---|---|---|---|
| 8,706,466 | B1 | 4/2014 | Klee |
| 8,718,778 | B2 | 5/2014 | Bikson et al. |
| 8,818,515 | B2 | 8/2014 | Bikson et al. |
| 8,903,494 | B2 | 12/2014 | Goldwasser et al. |
| 8,914,122 | B2 | 12/2014 | Simon et al. |
| 8,965,514 | B2 | 2/2015 | Bikson et al. |
| 9,302,107 | B2 | 4/2016 | Lauritzen et al. |
| 9,307,925 | B2 | 4/2016 | Russell et al. |
| 9,327,119 | B2 | 5/2016 | Skahan et al. |
| 9,339,642 | B1 | 5/2016 | Bikson et al. |
| 9,463,327 | B2 | 10/2016 | Lempka et al. |
| 2012/0265261 | A1* | 10/2012 | Bikson ............... A61N 1/36025 607/2 |
| 2013/0226261 | A1 | 8/2013 | Sparks et al. |
| 2013/0268019 | A1 | 10/2013 | Gupta et al. |
| 2015/0088223 | A1 | 3/2015 | Blum et al. |
| 2015/0112403 | A1 | 4/2015 | Ruffini et al. |
| 2015/0148869 | A1 | 5/2015 | Dorvall, II et al. |
| 2015/0174418 | A1 | 6/2015 | Tyler et al. |
| 2016/0055304 | A1* | 2/2016 | Russell ................. G16H 40/40 705/3 |
| 2016/0314282 | A1* | 10/2016 | Klee ....................... G06F 30/20 |

OTHER PUBLICATIONS

Butson et al., "Patient-Specific Analysis of the Volume of Tissue Activated During Deep Brain Stimulation," Neuroimage, 2007, vol. 34, pp. 661-670.

Datta et al., "Transcranial current stimulation focality using disc and ring electrode configurations: FEM analysis," J. Neural Eng. 2008, 5:163-174.

Datta et al., "Gyri-precise head model of transcranial direct current stimulation: Improved spatial focality using a ring electrode versus conventional rectangular pad," Brain Stimulation, 2009, 2:201 207e1.

Datta et al., "Individualized model predicts brain current flow during transcranial direct-current stimulation treatment in responsive stroke patient," Brain Stimulation, vol. 4, pp. 169-174, 2011.

Huang et al., Automated MRI segmentation for individualized modeling of current flow in the human head, J. Neural. Eng. 2013, vol. 10, pp. 1-26.

Kadosh, The Stimulated Brain: Cognitive Enhancement Using Non-Invasive Brain Stimulation, Academic Press, London, UK, 2014, see, in particular, Chapters 2 and 4, of the Kadosh text; Kindle Locations 1221-1897 and 2630-3326).

Kim et al., "Inconsistent outcomes of transcranial direct current stimulation (tDCS) may be originated from the anatomical differences among individuals: A simulation study using individual MRI data," Engineering in Medicine and Biology Society (EMBC), 2013 35th Annual International Conference of the IEEE, Jul. 2013, pp. 823-825.

Kirsh, et al., "Cranial Electrotherapy Stimulation for Treatment of Anxiety, Depression, and Insomnia," Psychiatr. Clin. N. Am., 36 (2013), pp. 169-176.

Klee, "Biology's built-in Faraday cages," Am. J. Phys., vol. 82, No. 6, 2014, pp. 451-459, n7.

Lefaucheur, "A comprehensive database of published tDCS clinical trials (2005-2016)," Clinical Neurophysiology, 2016, vol. 46, pp. 319-398.

Miranda et al., "Optimizing Electric-Field Delivery for tDCS: Virtual Humans Help to Design Efficient, Noninvasive Brain and Spinal Cord Electrical Stimulation," IEEE Pulse, vol. 8, Jul./Aug. 2017, pp. 42-45.

Parazzini et al., "A Computational Model of the Electric Field Distribution due to Regional Personalized or Non-Personalized Electrodes to Select Transcranial Electric Stimulation Target," IEEE Transactions on Biomedical Engineering, vol. 64, Jan. 2017, pp. 184-195.

Russell et al., "Individual differences in transcranial electrical stimulation current density," The Journal of Biomedical Research, 2013, vol. 27, pp. 495-508.

Russell et al., "Gender differences in current received during transcranial electrical stimulation," Frontiers in Psychiatry, Aug. 2014, vol. 5, pp. 1-7.

Song et al., "Numeric Investigation of Brain Tumor Influence on the Current Distributions During Transcranial Direct Current Stimulation," IEEE Transactions on Biomedical Engineering, vol. 63, No. 1, Jan. 2016, pp. 176-187.

Strickland, "A New Kind of Juice," IEEE Spectrum, vol. 53, Sep. 2016, pp. 34-40.

Makarov et al., Low-Frequency Electromagnetic Modeling for Electrical and Biological Systems Using MATLAB, Wiley, Hoboken, New Jersey, 2016, Chapters 1-6, 8-9, and 11-12, Kindle locations 1-381, 419-521, 587-689, and 797-817, hardcover pp. i-xviii, 1-255, 289-370, 423-505, and 591-598.

Chabay et al., Matter and Interactions, vol. II: Electric and Magnetic Interactions, 4th Edition, Wiley, Hoboken, New Jersey, 2015, Chapters 14 and 18, pp. i-xvi, 546-587, 716-764, and I-I10.

\* cited by examiner

Polarity Plots
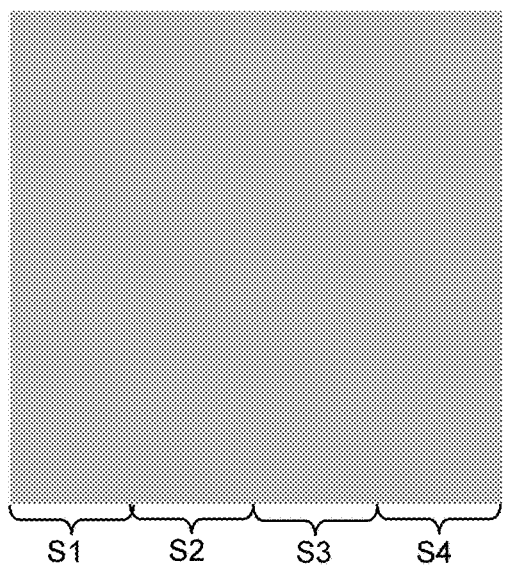
FIG. 5A — Base Case
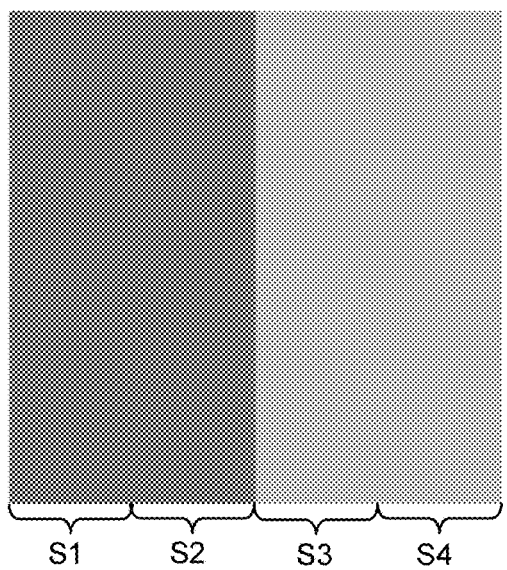
FIG. 5B — Diagonal Case
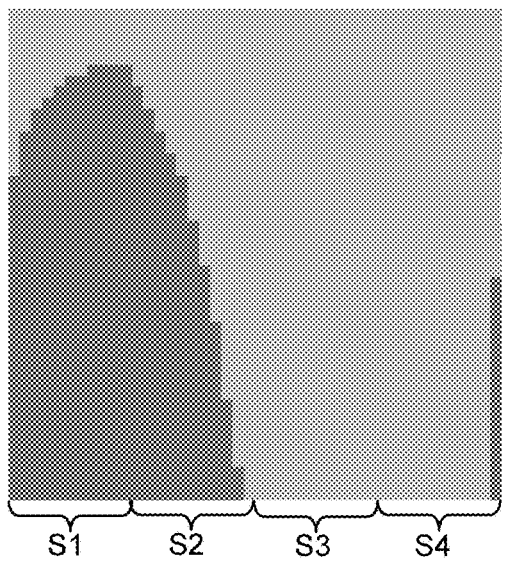
FIG. 5C — Glancing Case
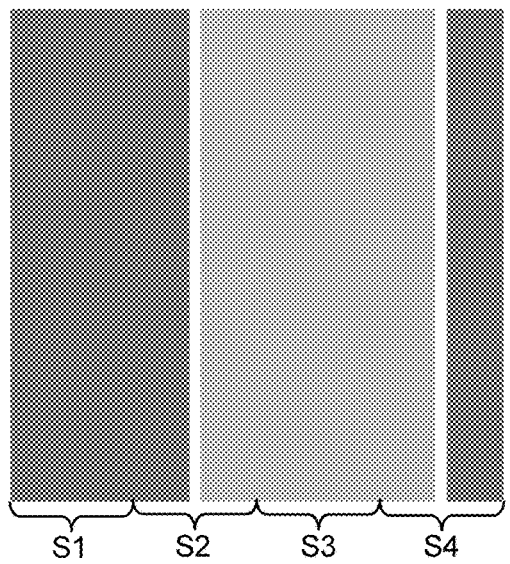
FIG. 5D — One-Sided Case

Polarity Plots

Base Case

Diagonal Case

Glancing Case

One-Sided Case

**Polarity Plots
One-Sided Case**

0.1 $\tau_{sigma}$ 1.0 $\tau_{sigma}$ 2.0 $\tau_{sigma}$ 3.0 $\tau_{sigma}$

Polarity Plots
One-Sided Case 4.0 $\tau_{sigma}$ 5.0 $\tau_{sigma}$ 6.0 $\tau_{sigma}$ 7.0 $\tau_{sigma}$

Polarity Plots
One-Sided Case

S5
0.1 $\tau_{sigma}$

S5
1.0 $\tau_{sigma}$

S5
2.0 $\tau_{sigma}$

S5
3.0 $\tau_{sigma}$

S5
4.0 $\tau_{sigma}$

NORMALIZED SULCUS CHARGE DISTRIBUTION

PAD ANODE AT L18; PAD CATHODE AT L40

NORMALIZED SULCUS CHARGE DISTRIBUTION

STRIP ANODE AT L18; PAD CATHODE AT L40

NORMALIZED SULCUS CHARGE DISTRIBUTION

POINT SOURCE ANODE AT PtSr; PAD CATHODE AT L40

RIGHT SULCUS FACE 13R

LEFT SULCUS FACE 13L

NORMALIZED SULCUS CHARGE DISTRIBUTION

NEIGHBORING CSF REGION (1x1x1 cm$^3$; D = 5 mm)

PAD ANODE AT L0; PAD CATHODE AT L40

NORMALIZED SULCUS CHARGE DISTRIBUTION

NEIGHBORING CSF REGION (1x1x4 cm$^3$; D = 5 mm)

PAD ANODE AT L0; PAD CATHODE AT L40

CHARGE-BASED METHODS FOR MODIFYING NEURAL ACTIVITY

CROSS-REFERENCE TO RELATED APPLICATION

This application claims the benefit under 35 USC § 119(e) of U.S. Provisional Application No. 62/412,328 filed on Oct. 25, 2016, the contents of which in its entirety is hereby incorporated by reference.

FIELD

This disclosure relates to the use of electrical stimulation to modify neural activity and, in particular, to the use of computed charge distributions on the bounding surfaces of sulci to select parameters for such stimulation including the locations of the electrodes used to apply the stimulation.

Definitions

As used in this specification and in the claims, the following terms and abbreviations and their associated plurals have the following meanings:

(1) "CSF" is cerebrospinal fluid.
(2) A "sulcus" (plural, sulci) is a groove, furrow, cleft, recess, or invagination that is (i) in the surface of a neural tissue and (ii) filled with CSF. In neuroanatomy texts and atlases, some grooves, especially deep grooves, are referred to as "fissures." To simplify the terminology of the specification and claims, the term "sulcus" is used broadly to include any groove, furrow, cleft, recess, or invagination that is in the surface of a neural tissue and filled with CSF irrespective of the particular term used in the neuroanatomy literature for the structure, e.g., as used herein, fissures are sulci.
(3) A "CSF charge distribution" is a computed charge distribution on a bounding surface of a sulcus or a portion thereof, the computation being performed using a computer.
(4) An "anode" is a positive electrode which when in a conductive medium applies a flow of positive current to the medium.
(5) A "cathode" is a negative electrode which when in a conductive medium removes a flow of positive current from the medium.
(6) A "pixel" (also referred to herein as a "2D pixel" or a "surface pixel") is a closed area of a surface. Pixels are two dimensional and can have a variety of shapes, e.g., square, triangular, or hexagonal shapes. Pixel sizes and shapes can be the same or can vary for a given surface and/or between different surfaces.
(7) The "'379 application" refers to U.S. patent application Ser. No. 15/097,379 filed Apr. 13, 2016, and entitled "Computer-Implemented Tools for Use in Electrophysiology," the contents of which in their entirety are incorporated herein by reference. The '379 application was published as U.S. Patent Application Publication No. US 2016/0314282 A1 (the "'282 publication") on Oct. 27, 2016.

BACKGROUND

The use of electrical stimulation to modify neural activity is both an old and an extensive field of scientific, engineering, and clinical activity. Historically, the parameters for the stimulation, including the locations of the electrodes used to apply the stimulation, were determined by trial and error. In many cases, this approach is still used today.

Although electrical stimulation of sufficient strength normally produces a physiological response, the responses are not always consistent or repeatable between practitioners. With the goal of explaining/understanding this variability, efforts have been made to analyze/predict the response of neural tissues to electrical stimulation from an electromagnetic field theory point of view.

As a result of these efforts, the present state of the art uses a combination of (1) tissue geometry and electrical properties obtained from, for example, CT and MRI images including diffusion tensor magnetic resonance images, and (2) electric field distributions and their associated current density distributions obtained from computer simulations. Based on these inputs, clinicians and researchers have become better able to select stimulation parameters, including electrode locations, for invasive procedures that use electrodes within the body (e.g., deep brain and spinal cord stimulation), non-invasive procedures that use electrodes located on the surface of the body (e.g., transcranial brain stimulation, transcutaneous spinal cord stimulation, and transcutaneous peripheral nerve stimulation), and systems that use combinations of internal and surface electrodes.

Examples of the broad range of electrical stimulation protocols and techniques that have been the subject of patents and patent applications include: U.S. Pat. No. 9,339,642 assigned to Soterix Medical, Inc., and entitled "System and Method for Conducting Multi-Electrode Electrical Stimulation;" U.S. Pat. No. 9,327,119 assigned to Vision Quest Industries Incorporated and entitled "Electrostimulation System;" U.S. Pat. No. 9,302,107 assigned to Second Sight Medical Products, Inc., and entitled "Cortical visual prosthesis;" U.S. Pat. No. 8,914,122 assigned to Electrocore, LLC, and entitled "Devices and Methods for Non-Invasive Capacitive Electrical Stimulation and their Use for Vagus Nerve Stimulation on the Neck of a Patient" U.S. Pat. No. 8,903,494 assigned to Thync, inc., and entitled "Wearable Transdermal Electrical Stimulation Devices and Methods of Using Them;" U.S. Pat. No. 8,818,515 assigned to the City University of New York and entitled "Voltage Limited Neurostimulation;" U.S. Pat. No. 7,684,866 assigned to Advanced Neuromodulation Systems, Inc., and entitled "Apparatus and Methods for Applying Neural Stimulation to a Patient" U.S. Pat. No. 7,340,299 assigned to Emory University and entitled "Methods of Indirectly Stimulating the Vagus Nerve to Achieve Controlled Asystole;" U.S. Patent Application Publication No. 2016/0055304 assigned to Aaken Laboratories and entitled "Targeted Electrical Stimulation;" U.S. Patent Application Publication No. 2015/0174418 assigned to Thync, inc., and entitled "Device and Methods for Noninvasive Neuromodulation Using Targeted Transcranial Electrical Stimulation;" and U.S. Patent Application Publication No. US 2015/0112403 assigned to Neuroelectrics Barcelona S. L. and entitled "Method and a System for Optimizing the Configuration of Multisite Transcranial Current Stimulation and a Computer-Readable Medium." The recent text *The Stimulated Brain: Cognitive Enhancement Using Non-Invasive Brain Stimulation*, Academic Press, London, U K, 2014, edited by Roi Cohen Kadosh (hereinafter the "Kadosh text"), discusses the extensive scientific literature regarding the use of non-invasive electrical stimulation to modulate brain activity, including the use of computer modeling in this effort (see, in particular, Chapters 2 and 4, of the Kadosh text; Kindle Locations 1221-1897 and 2630-3326). The contents of the foregoing references, as well as those cited below in this section and in the Detailed Description, are hereby incorporated herein by reference in their entireties as examples of the existing state of the art. The references are also individually and specifically incorporated by reference herein for the material contained in them that is discussed in the sentence or paragraph in which the reference is cited.

The standard method for performing computer simulations used in selecting stimulation parameters is the finite element method (FEM) for which both open source and commercial software packages are available, e.g., the COMSOL Multiphysics Finite Element Analysis Software (previously FEMLAB) distributed by COMSOL, Inc., Burlington, Mass. See, for example, U.S. Pat. No. 8,180,601 assigned to the Cleveland Clinic Foundation and entitled "Systems and Methods for Determining Volume of Activation for Deep Brain Stimulation." The output provided to the clinician or researcher is often a pseudocolor image of the neural tissue, e.g., the brain, showing distributions of electric fields and/or their associated current densities within the tissue. The clinician or researcher can adjust stimulation parameters (e.g., by moving electrodes, selecting electrodes from a set of electrodes, and/or changing electrode montages) and examine the effects of the adjustments on the field/current distributions. In this way, the computer simulations become part of the ultimate decision on the stimulation protocol used to modify neural activity.

SUMMARY

In accordance with the present disclosure, instead of, or in addition to, computed electric fields and their associated current densities, one or more CSF charge distributions, as defined above, are used in selecting stimulation protocols and techniques for modifying neural activity.

Compared to field/current distributions, as well as potential distributions, CSF charge distributions have a number of advantages. One primary advantage is the fact that the distributions focus on cerebrospinal fluid. Cerebrospinal fluid normally has very few cells and thus its electrical behavior is not complicated by the presence of cellular membranes with their high resistance and capacitance. Also, cerebrospinal fluid is generally the neural material with the highest conductivity. As such, cerebrospinal fluid plays a defining role in the response of neural tissues to electrical stimulation. Providing clinicians and researchers with CSF charge distributions thus aids in providing insight into the phenomena underlying physiological responses to electrical stimulation.

CSF charge distributions are also intuitively easy to understand. One can readily envisage accumulations of charge (positive or negative) at particular locations on the bounding surfaces of CSF structures. The interaction of charged molecules (neurotransmitters) with receptors located on the bounding surface of a biological conductor is also one of the basic mechanisms of neural activity. Accordingly, analyzing/predicting the effects of electrical stimulation using CSF charge distributions allows a clinician/researcher to tie electrical stimulation to an endogenous mechanism of neural function.

Further, when CSF charge distributions are expressed as charge per surface pixel (also referred to herein as "charge per pixel" or "charge/pixel"), the surface pixels can be viewed as sensors that see (sense) charges both in front of and behind the pixel and then adjust their charge based on the charges they sense. As such, intuitive understandings of the origins of particular charge distributions are easily generated (see below), something that is not possible with electric potentials, electric fields, or current densities.

Also, electrical potentials, electric fields, and current densities do not interact with one another, e.g., the electric field at one spatial location does not interact with (does not change) the electric field at another spatial location. In direct contrast, surface charges at different spatial locations do interact with one another since, as discussed immediately above, each portion of a surface (e.g., each surface pixel when the surface is divided into pixels) "senses" the charges at other locations in space. Consequently, surface charges exhibit a feedback mechanism by which they interact with one another to eventually reach a steady state configuration. FIGS. 10-12 below illustrate representative examples of the types of interaction and feedback effects that can occur. This interaction/feedback mechanism exhibited by CSF charge distributions is another way in which CSF charge distributions enhance the ability of clinicians/researchers to understand the effects of electrical stimulation on neural activity and thereby select electrode locations that achieve desired physiological responses.

A further advantage of CSF charge distributions is that when expressed in terms of charge per surface pixel, as a general rule, the distributions do not change with a change in scale (see paragraphs [0056]-[0060] of the '379 application; paragraphs [0064]-[0068] of the '282 publication). That is, the distributions depend on system geometry, but not system size. Accordingly, once a clinician or researcher develops an understanding for a CSF charge distribution associated with a particular system geometry, he/she can use that understanding to predict/analyze CSF charge distributions for the same or similar systems of different sizes, e.g., individuals with different size brains.

In direct contrast, potential and electric field distributions do change with a change in scale, the potential distribution varying as one over the scale and the electric field distribution varying as one over the square of the scale, e.g., if the size of the system doubles with the primary sources held constant, the signs of the potentials remain constant but their magnitudes decrease by a factor of two and the directions of the electric fields remain the same but the magnitudes of the fields decrease by a factor of four. CSF charge distributions expressed in terms of charge per surface pixel are invariant to such a change in scale, e.g., for the same number and same relative locations of the pixels used to simulate the system, the charge per pixel does not change for a doubling (or any other change) of the size of the system.

Finally, CSF charge distributions are easier to display than electric fields or current density fields since charge distributions are scalars while electric fields and current densities are vectors. Electric fields are often displayed using pseudocolor images showing their magnitudes. See, for example, FIGS. 4.4, 4.5, and 4.7 of the Kadosh text. Those images do not tell the viewer the direction of the field. A pseudocolor image of a CSF charge distribution, on the other hand, can easily inform the viewer of both the magnitude and the sign of the charges by assigning a series of colors to positive charges and a different series of colors to negative charges, with the individual colors in each case representing different magnitudes. Indeed, as illustrated in FIGS. 5-6 and 10-11 below, even black-and-white polarity plots provide substantial amounts of information regarding CSF charge distributions to a viewer.

In view of these considerations, the present disclosure provides a method for applying electrical current to a neural tissue using at least two electrodes, the neural tissue having at least one sulcus filled with cerebrospinal fluid, the method comprising:

(a) selecting a location for at least one of the electrodes relative to a location of a sulcus of the neural tissue by calculating, using a computer, a charge distribution for at least a part of the bounding surface of the sulcus, said charge distribution originating at least in part from charges on at least part of the electrode; and (b) applying electrical current to the neural tissue using an electrode substantially at the location selected in step (a).

Additional aspects and advantages of the technology disclosed herein are set forth in the detailed description that follows, and in part will be readily apparent to those skilled in the art from that description or recognized by practicing the technology as described herein. The accompanying drawings are included to provide a further understanding of the technology, and are incorporated in and constitute a part of this specification. It is to be understood that the various aspects of the technology disclosed in this specification and in the drawings can be used individually and in any and all combinations. It is also to be understood that the general description set forth above and the detailed description which follows are merely exemplary of the invention and are intended to provide an overview or framework for understanding the nature and character of the invention as defined by the claims.

BRIEF DESCRIPTION OF THE DRAWINGS

FIGS. 5A, 5B, 5C, and 5D are plots illustrating CSF charge distributions, specifically, the figures are polarity plots at steady state of the S1, S2, S3, and S4 surface charges for, respectively, the base case, the diagonal case, the glancing case, and the one-sided case. In these figures and in FIGS. 6, 10 and 11, the lighter shaded areas have charge with a positive polarity, the darker shaded areas have charge with a negative polarity, and the un-shaded areas are uncharged.

FIG. 10A is for a time of 0.1 $\tau_{sigma}$, FIG. 10B for 1.0 $\tau_{sigma}$, FIG. 10C for 2.0 $\tau_{sigma}$, FIG. 10D for 3.0 $\tau_{sigma}$, FIG. 10E for 4.0 $\tau_{sigma}$, FIG. 10F for 5.0 $\tau_{sigma}$, FIG. 10G for 6.0 $\tau_{sigma}$, and FIG. 10H for 7.0 $\tau_{sigma}$, where $\tau_{sigma}=\varepsilon_0/\sigma$. In Example 1 and thus for the plots of these figures, $\sigma$ and $\tau_{sigma}$ for CSF were $\sigma=1.8$ S/m and $\tau_{sigma}=4.9\times10^{-12}$ seconds. The asterisk in these figures identifies the pixel of the S2 portion of the bounding surface whose charge is plotted in FIG. 12.

FIG. 11A is for a time of 0.1 $\tau_{sigma}$, FIG. 11B for 1.0 $\tau_{sigma}$, FIG. 11C for 2.0 $\tau_{sigma}$, FIG. 11D for 3.0 $\tau_{sigma}$, and FIG. 11E for 4.0 $\tau_{sigma}$. The asterisk in these figures identifies the pixel of the S5 portion of the bounding surface whose charge is plotted in FIG. 12.

DETAILED DESCRIPTION

Figure 1:
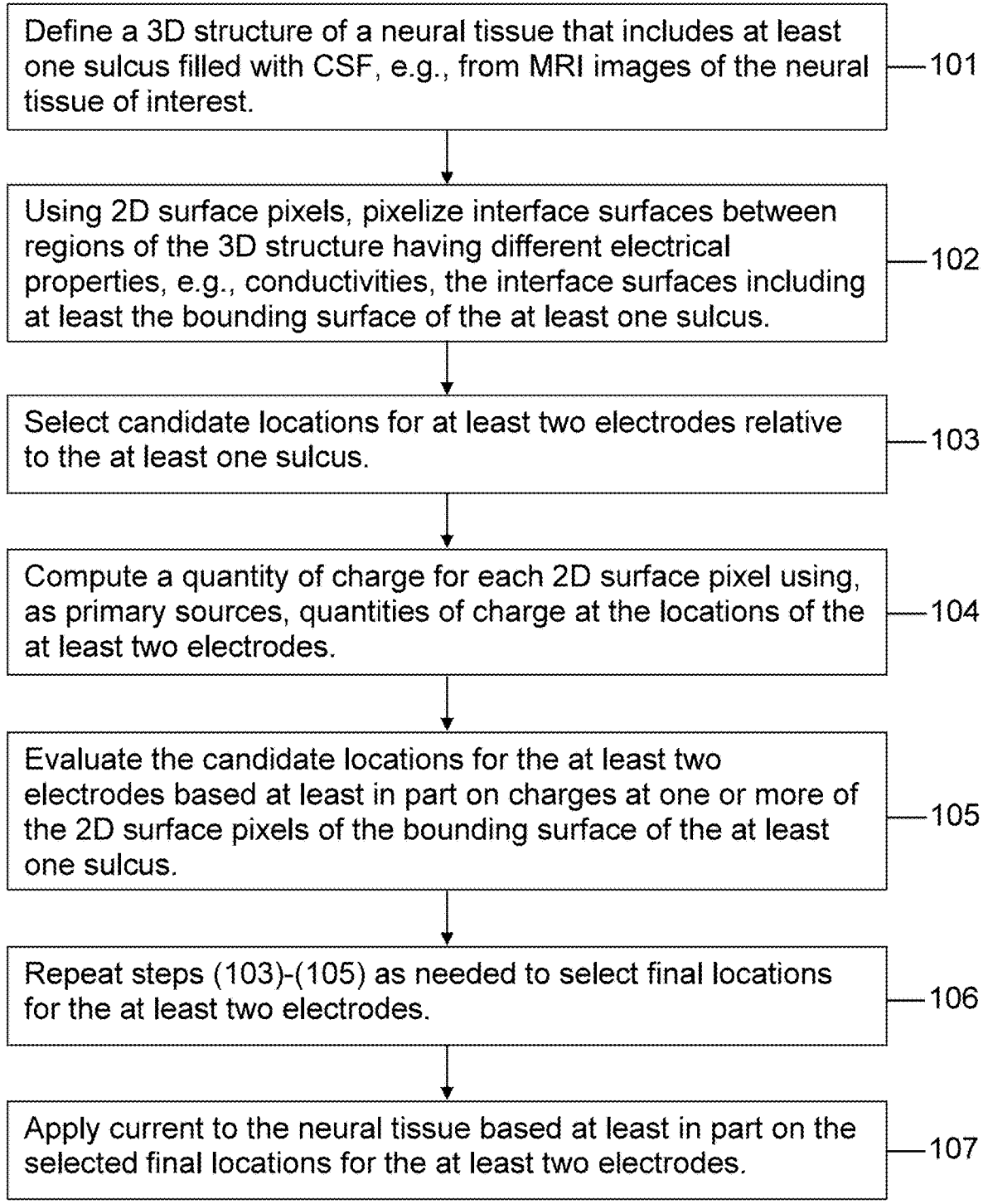
FIG. 1 is a flowchart illustrating an exemplary embodiment of the present disclosure.

FIG. 1 is a flowchart of an embodiment of the present disclosure showing an exemplary process for using a computed charge distribution on a bounding surface of a sulcus or a portion thereof to select electrode locations for applying electrical current to a neural tissue to modify neural activity.

The process begins in step 101 with a definition of a three dimensional (3D) structure for a neural tissue that includes at least one sulcus filled with CSF, e.g., all or, more typically, a portion of the brain and/or the spinal cord. The 3D structure may be the same as or larger than the neural tissue of interest. For example, if the clinical goal is to use electrical stimulation to ameliorate the effects of a stroke on motor function, the neural tissue of interest whose activity is to be modulated may be a portion of the motor cortex, but the 3D structure may need to be larger in order to take into account quantities of charge that accumulate at other locations in the brain as a result of the electrical stimulation. Similarly, for electrical stimulation applied to the spinal cord to alleviate pain, the 3D structure may need to extend beyond the particular portion of the spinal cord to which current is to be applied.

The spatial extent of the 3D structure will also depend on the locations of the electrodes used to apply the stimulating current and whether the current is applied invasively or non-invasively. Smaller spatial extents can generally be used for invasive stimulation and/or for relatively small spacings between anode(s) and cathode(s). Current applied non-invasively to, for example, the surface of the scalp or the skin overlying the spinal cord can spread widely when a remote return electrode is used. Accordingly, there may be a need to use relatively large 3D structures to include the effects of quantities of charge distant from the neural tissue of interest. For relatively closely-spaced electrodes, the quantities of charges on the electrodes themselves and the quantities of charges on nearby interfaces between regions having different electrical properties, e.g., conductivities and/or relative dielectric constants, tend to dominate, thus allowing CSF charge distributions to be computed using somewhat smaller 3D structures.

For clinical applications, 3D structures obtained from MRI, DTI, CT, and similar imaging technologies may be used in computing CSF charge distributions. An extensive literature has been developed relating to discretizing data obtained from imaging technologies for use in subsequent electromagnetic field calculations, i.e., FEM calculations in the prior art. A representative example is U.S. Pat. No. 9,307,925 assigned to Aaken Laboratories and entitled "Methods and Systems for Generating Electrical Property Maps of Biological Structures." See also the references cited above in the Background section of this disclosure and FIG. 4.3 and the discussion of that figure in the Kadosh text. Typically, the 3D neural structures are defined in terms of the surfaces that separate different components of the neural tissue, e.g., the surfaces (interfaces) between skin, bone, meninges, CSF, white matter, gray matter, etc. Importantly for the present disclosure, CSF has a distinctive signature in the imaging techniques used with neural tissue and thus the bounding surfaces of sulci are readily identified in these images. Although subject-specific 3D images are generally preferred, if such images are unavailable or too costly, neuroanatomy texts and atlases, including digital atlases, can be used in step 101.

Step 102 uses the 3D structure defined in step 101 to form the pixelized surfaces employed in step 104 to compute CSF charge distributions. The pixelization can be performed using meshing techniques of the type employed in, for example, CAD and similar graphical displays. In general terms, each surface pixel is characterized by (i) a geometry, e.g., a square, triangular, or hexagonal shape, (ii) a size, and (iii) a normal, e.g., a normal extending from a bounding surface of a sulcus into the sulcus's CSF. Although a pixel size is needed for any particular computation, as discussed above, when expressed as charge/pixel, CSF charge distributions scale so that a convenient pixel size can be employed in the computations and then the output scaled to, for example, match the actual size of the neural tissue of interest.

As discussed below, the $\Omega\delta\rightarrow 0$ processes of the '379 application are preferably used in step 104. In those processes, 3D calculation cells are flattened into 2D calculation cells (hence the $\delta\rightarrow 0$ nomenclature). Each 2D calculation cell (each 2D pixel) is characterized by its solid angles ($\Omega$ values) as seen from all other 2D calculation cells (2D pixels) and from the charges associated with internal electrodes used to apply current to the neural tissue.

As noted in the '379 application, for some simulations, flattened calculation cells can be used in combination with non-flattened calculation cells. For example, at the locations of source charges, three dimensional calculation cells, e.g., cubic calculation cells, can be used so that free charge changes at those locations are determined using the same calculation process, e.g., the solid angle process, as used at interfaces between materials having different electrical properties. Three dimensional calculation cells can also be useful in simulating an anisotropic medium since the conductivity values and/or the relative dielectric constants for the faces of the calculation cells can be selected to account for the anisotropicity of the medium. Also, when the system being simulated includes non-conservative fields acting at an interface, three dimensional calculation cells can be used on either side of the interface. In such cases, each 2D calculation cell of the $\Omega\delta\rightarrow 0$ processes will also be characterized by its solid angles as seen from the charges of the 3D calculation cells.

In step 103, candidate locations for at least two electrodes relative to at least one sulcus are selected. Such selection can include selecting the types/configurations of the electrodes to be used in step 107. For example, for an electrode having an extended surface area over which current can enter/leave biological tissue, multiple point sources distributed over the spatial extent of the electrode may be used as candidate electrode locations in the computations (simulation) of step 104.

Various strategies can be used in selecting candidate locations based on the desired physiological response. For example, in the case of transcranial stimulation, it may be desirable to produce a CSF charge distribution on the bounding surface of a particular sulcus associated with gyri known to be involved in a biological state or function of interest, e.g., motor control, speech, mood, arousal, or the like. Work at the City University of New York (CUNY) has explored a number of strategies and protocols for locating electrodes on the head of a subject (e.g., a patient) during transcranial stimulation. See U.S. Pat. No. 8,494,627 entitled "Neurocranial Electrostimulation Models, Systems, Devices, and Methods," U.S. Pat. No. 8,718,778 entitled "Apparatus and Method for Neurocranial Electrostimulation," and U.S. Pat. No. 8,965,514 entitled "Transcranial Stimulation."

Similarly, work at the Cleveland Clinic has developed strategies and protocols for locating electrodes used in deep brain stimulation, as well as for designing electrode structures to achieve desired physiological responses. See, for example, U.S. Pat. No. 7,346,382 entitled "Brain Stimulation Models, Systems, Devices, and Methods" and U.S. Pat. No. 8,538,543 entitled "System and Method to Design Structure for Delivering Electrical Energy to Tissue." See also U.S. Patent Application Publication No. US 2015/0148869 assigned to the University of Utah Research Foundation and entitled "Charge Steering High Density Electrode Array;" U.S. Patent Application Publication No. US 2013/0268019 assigned to Medtronic, Inc., and entitled "Electrical Stimulation Programming;" and U.S. Patent Application Publication No. 2013/0226261 assigned to Intelect Medical, Inc., and entitled "Clinician Programmer System and Method for Generating Interface Models and Displays of Volumes of Activation." Strategies for electrode placement for spinal cord stimulation have also been developed. See, for example, U.S. Pat. No. 9,463,327 assigned to the Cleveland Clinic and entitled "Systems and Methods for Determining Effective Stimulation Parameters."

The candidate electrode locations of step 103 can be selected using techniques of the types discussed in these patents and patent applications, and/or other techniques known in the literature or found to be particularly efficacious in producing desired CSF charge distributions.

As noted above in connection with the discussion of pixelization step 102, computation step 104 is preferably performed using the $\Omega\delta\rightarrow 0$ processes of the '379 application. As illustrated in, for example, Example 2 of that application, these processes produce accurate charge distributions even for a coarse descretation of an object's surface, i.e., for a relatively low number of 2D surface pixels. The $\Omega\delta\rightarrow 0$ processes of the '379 application are an example of the "charge first" process disclosed in Klee, U.S. Pat. Nos. 8,180,617 and 8,706,466, entitled "Computer-Based Computational Tools for Use in Electrophysiology." In accordance with the charge first process, charge distributions are computed directly without first calculating a potential distribution and then taking its spatial derivative. This improves both efficiency and accuracy. That said, if desired, step 104 can be performed without using a charge first process by first computing a potential distribution and then taking a spatial derivative of that distribution.

It should be noted that the amount of current applied through the at least two electrodes normally affects only the magnitude of the charges of the CSF charge distribution and not the distribution itself, i.e., for linear or substantially linear materials, the magnitudes scale with the amount of current applied through the anode(s) and removed through the cathode(s). Hence, step 104 can be performed with an arbitrary amount of current and then scaled to the particular amount of current used in step 107, that amount being selected based on safety and efficacy considerations such as those discussed in the patents and applications referenced above in connection with step 103.

In step 105, the candidate locations for the electrodes are evaluated using all or a part of the CSF charge distribution computed in step 104. For example, it may be desirable to use electrical stimulation to accumulate positive or negative charges at a particular location on the bounding surface of a particular sulcus, and in such case, the candidate locations for the electrodes will be evaluated to determine whether such a desired charge accumulation has been achieved. At the same time, the CSF charge distribution on the same sulcus or other sulci (and/or charge distributions on other neural structures computed during the simulation) may be examined to determine if undesired accumulations of charges (positive or negative) can be expected to result from the candidate locations for the electrodes.

If desired, computed charge distributions can be used to calculate and/or estimate voltage distributions, electric field distributions, and/or current density distributions and those distributions used in the evaluation of step 105. The transformation from a charge distribution to a voltage or electric field distribution can be performed by applying the superposition principle at the field point or points at which voltage values or electric field magnitudes and directions are desired. Specifically, at each field point, using Coulomb's law, the voltage/electric field resulting from the charges of each surface pixel and each internal electrode are calculated and then summed to give the overall voltage/electric field for the charge distribution at the field point. A current density distribution can then be obtained from the electric field distribution using Ohm's law, e.g., by multiplying the calculated electric field by the conductivity at the field point. As a further alternative, in for example the case of deep brain stimulation, the computed charge distributions and/or voltage, electric field, and/or current density distributions derived therefrom can be used with a neuron model, such as the NEURON software program available at Yale University and Duke University, to compute a volume of activation (VOA) (also known as a volume of tissue activation (VTA)) for the selected candidate electrode locations. See, for example, U.S. Patent Application Publication No. US 2015/0088223 assigned to Boston Scientific Neuromodulation Corporation and entitled "VOA Generation System and Method Using a Fiber Specific Analysis." Combinations of evaluation methods can be employed if desired. Similarly, as indicated in step 106, multiple candidate locations for the electrodes can be evaluated by repeating steps 103-105 one or more times as needed until a final set of locations for the electrodes is achieved.

Normally, the evaluation of step 105 will be facilitated by displaying a CSF charge distribution or a portion thereof, or a parameter value derived from such a distribution, e.g., the total amounts of positive and negative charge accumulated on one or more portions of the bounding surface of a sulcus as illustrated in FIG. 4 discussed below. When displaying charge distributions expressed as charge per pixel, if the pixel sizes and/or shapes vary on a given surface and/or between surfaces, it may be helpful to convert to charges per unit area so that the clinician/researcher can more easily compare the amounts of charges in different regions of a surface and/or between surfaces.

A particularly useful display for use in step 105 is to plot charge polarities for a sulcus's bounding surface without regard to magnitudes as illustrated in FIGS. 5, 6, and 10-11 discussed below. In addition to their intrinsic value of being easy to understand, polarity plots can be used to estimate the normal electric field in the neural tissue surrounding a sulcus and from that normal electric field, the normal current density can be estimated using the conductivity of the surrounding tissue.

Specifically, for a CSF conductivity substantially greater than that of the surrounding tissue (the typical case), at steady state, the normal electric field in the CSF will be small so that the jump in normal electric field at the bounding surface due to the presence of charge at that surface will be primarily in the surrounding tissue. If, as shown by a polarity plot, the charge is positive at a particular location on the bounding surface of a sulcus, the normal electric field can be estimated as pointing into the surrounding tissue, while if it is negative, it can be estimated as pointing out of the surrounding tissue.

As illustrated in FIGS. 10-11, polarity plots can also be used to illustrate changes in the polarity of particular portions of a sulcus's bounding surface as a function of time. Based on such plots, the time course of the current applied through the stimulating electrodes can be selected to achieve desired physiological effects, e.g., polarity plots can be used in selecting, for example, stimulation frequencies, pulse widths, pulse rates, and the like. The time course of the surface charges at one or more pixels can also be used for this purpose as illustrated in FIG. 12.

Figure 7:
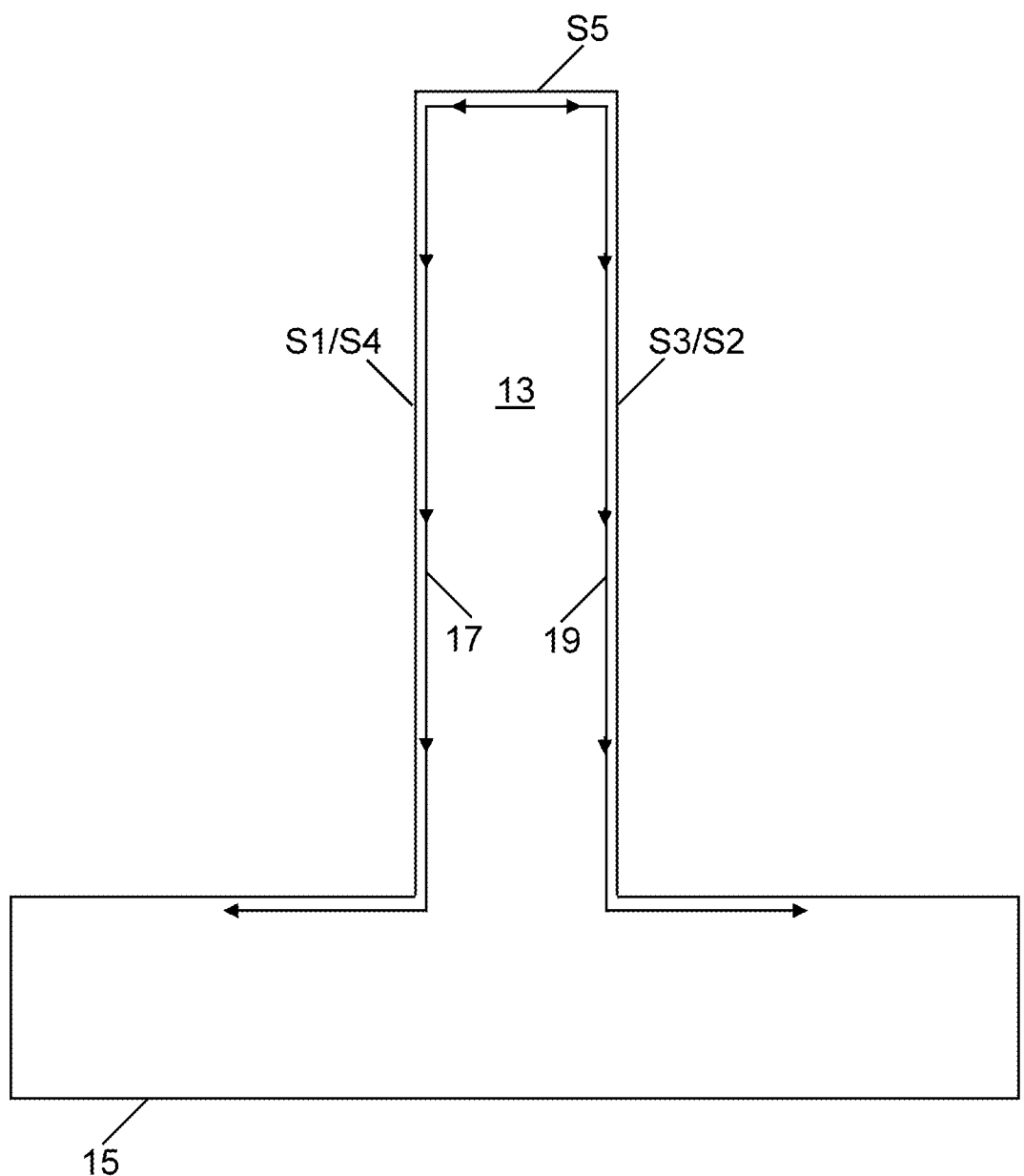
FIG. 7 is a mid-plane cross-sectional view of the sulcus geometry of FIG. 2 illustrating the paths of the trace plots of FIGS. 8 and 9.

As a further way of displaying the results of the computations of step 104, traces across the bounding surface of a sulcus can be used. FIGS. 7-9 illustrate this approach. As another alternative, pseudocolor, including black and white, 3D charge distribution plots can be used to show locations of charge accumulation (positive and/or negative).

A particularly effective way of evaluating surface charge distributions in step 105 is to analyze/interpret the distribution in terms of each surface pixel acting as a "sensor" that looks out into the world of surrounding charges, i.e., the world of surface charges at other pixels and charges at the electrodes (the applied sources). The surface pixel senses the fields of surrounding charges both in front of it and behind it, and for each surrounding charge, ignores everything between the pixel and the surrounding charge, i.e., the pixel senses the Coulomb electric field of each surrounding charge irrespective of what may be between the surrounding charge and the pixel.

Some surrounding charges can be sensed well and others cannot be sensed at all depending on the solid angle of the sensing pixel as seen from the surrounding charge, i.e., if the solid angle of the sensing pixel as seen from the surrounding charge is close to $2\pi$ steradians, the surrounding charge is sensed well, while if the solid angle is close to zero or zero, the surrounding charge is sensed poorly or not at all. The surface pixel acting as a sensor adds up the effects of the surrounding charges based on their strengths and how well they are sensed, and adjusts its charge based on the electrical properties of the media on either side of the pixel and the electrical flux acting at the pixel. The same summation occurs at all of the pixels and through feedback between the pixels, the system arrives at its steady state surface charge distribution.

Treating pixels as sensors brings into play the common knowledge of how sensors, e.g., optical sensors, work. Through this approach, complex surface charge distributions can be readily analyzed/interpreted by looking at particular parts of the distribution and asking what a pixel sensor would see if located at that part. If the pixel sensor would see mainly positive surrounding charges in front of its higher conductivity side or mainly negative surrounding charges behind its higher conductivity side or combinations thereof, its surface charge will be positive and vice versa for negative charges in front and/or positive charges behind the pixel's higher conductivity side.

If positive surrounding charges are both in front of and behind the pixel sensor's higher conductivity side, the surface charge at the sensor pixel will depend on the magnitudes of those surrounding charges and the ability of the sensor pixel to sense the charges, i.e., the solid angle of the sensor pixel as seen from the various surrounding charges. Similar considerations apply to the case of negative surrounding charges both in front of and behind the pixel sensor's higher conductivity side, as well as to combinations of positive/negative charges in front of and/or behind the higher conductivity side.

It should be noted that the phrases "in front of" and "behind" include but are not limited to charges directly in front of or directly behind the pixel being considered, but include charges off to the side of the pixel that are in front of or behind the plane of the pixel. Charges that are in the plane of the pixel have no effect on the pixel because they cannot be seen (sensed) by the pixel, the solid angle of the pixel for such in-plane charges being zero, i.e., the pixel is so oblique to the charges that it cannot sense the charges at all.

In addition to its use in analyzing/interpreting computed surface charge distributions the pixel-as-a-sensor process can also be used to predict/estimate surface charge distributions through considerations of: (i) the locations of the primary charges of the electrodes, (ii) the surface charges such primary charges will seek to induce, and (iii) the interactions between the surface charges thus induced. Likewise, the process can be used to predict/estimate the effects on a computed surface charge distribution of a change in the location of one or more primary charges and/or a change in a primary charge montage, e.g., by splitting a single electrode (anode and/or cathode) into multiple electrodes, without the need for a full recalculation of the surface charge distribution. The ability of the pixel-as-a-sensor process to analyze/interpret computed surface charge distributions and estimate/predict the changes likely to result to those distributions from changes in electrode locations/configurations is a major advantage of the use of computed surface charge distributions in the selection of electrode locations for modifying neural activity through electrical stimulation. Computed potential, electrical field, and current density distributions do not provide this advantage.

In addition to the effects due to the locations, signs, and magnitudes of the surrounding charges, the magnitude of the charge at the sensor pixel will depend on the difference in conductivity between the higher and lower conductivity sides of the sensor pixel. The largest magnitude will occur when the lower conductivity side is a non-conductor. This magnitude will drop as the difference becomes smaller, eventually becoming zero when the conductivity is the same on both sides of the sensor pixel. This effect can be seen from, for example, Eqs. (33), (37), (39), and (41) of the '379 application where the charge at a surface pixel varies as $\sigma_{diff}/\sigma_{sum}$, where $\sigma_{diff}$ is the difference between the higher and lower conductivities on the two sides of the pixel and $\sigma_{sum}$ is the sum of those conductivities. When the lower conductivity is zero, this ratio becomes 1.0 and thus the charge at the sensor pixel is independent of the magnitude of the higher conductivity.

The use of the pixel-as-a-sensor process to evaluate CSF charge distributions is demonstrated below in connection with the examples of FIGS. 2-12 and, in particular, the polarity plots of FIGS. 5-6 and 10-11. It is also applied to the charge distributions and charge/pixel values of FIGS. 15-25.

Once steps 101 through 106 are completed, step 107 is performed in which current is applied to the neural tissue based at least in part on the selected final electrode locations of step 106. The electrode locations used in step 107 need not be identical to those selected in step 106 and, in general, will not be identical as a result of constraints such as subject comfort, the amount of hair at the selected location, subject-specific abnormalities at the selected location, and the like, as well as variations in electrode placement between practitioners. Rather, in step 107, the electrodes are placed at substantially the location selected in step 106, i.e., within an area or volume that is ±25% (preferably within ±20%, most preferably within ±10%) of the relevant area or volume in which the electrode could be placed. For example, for deep brain stimulation, the relevant volume may be the volume of the subject's brain or a portion thereof, e.g., a particular nucleus, and for transcranial stimulation, the relevant area may be the surface area of the subject's scalp or a portion thereof, e.g., an area corresponding to a particular lobe of the cerebral cortex.

It will be understood, of course, that the phrase "final locations" as used in steps 106 and 107 does not represent immutable locations for the electrodes but merely the culmination of a particular application of the process of FIG. 1. Thus, the steps of FIG. 1 may and, in general, will be repeated based on the physiological responses from one or more applications of those steps for an individual subject or between subjects. For example, as a result of an initial application of these steps, a practitioner may conclude that the 3D structure of step 101 for a particular subject needs to be refined and may order further MRI or other types of images. Similarly, as a result of applying current to the neural tissue at the selected locations of step 106, the practitioner may observe undesirable side effects which the practitioner may desire to ameliorate through the selection of a different candidate location for the electrodes in step 103. In these and similar cases, the method of FIG. 1, or particular steps of that method, can be repeated one or more times to optimize the electrode locations for a particular subject or a particular class of subjects. Similarly, in some cases, it may be desirable to perform only a subset of the steps of FIG. 1, e.g., steps 101-104 with the output of performing the steps being, for example, a graphical display of a CSF charge distribution computed in step 104.

The steps set forth in the flowchart of FIG. 1 or in other flowcharts developed based on the present disclosure can be readily implemented using a variety of computer equipment and a variety of software programming languages, e.g., FORTRAN, which is well-suited for scientific calculations. In this regard, as is typical for scientific calculations, the charge distributions will normally be determined in at least double precision. Other programming languages that can be used in the practice of the disclosure include, without limitation, BASIC, PASCAL, C, C++, PYTHON, and the like. More than one programming language can be used in the practice of the disclosure if desired.

Output from the computations can be in electronic and/or hard copy form, and can be displayed in a variety of formats, including in tabular and graphical form. For example, graphs, including topographical graphs, can be prepared using commercially available data presentation software such as MICROSOFT's EXCEL program and/or R.

Programs for implementing the disclosure can be provided to users on a non-transitory computer-readable medium with instructions stored thereon that, when executed by a processor, perform the steps of the process. Non-limiting examples of such media include diskettes, CDs, flash drives, and the like. The programs can also be downloaded to users through the internet. In addition, the process of the disclosure can be provided to users on-line through, for example, "cloud" computing. The process can be performed on various computing platforms, including personal computers, workstations, mainframes, supercomputers, etc.

Without intending to limit its scope in any manner, the disclosure is further illustrated by the following examples.

Example 1

Figure 2:
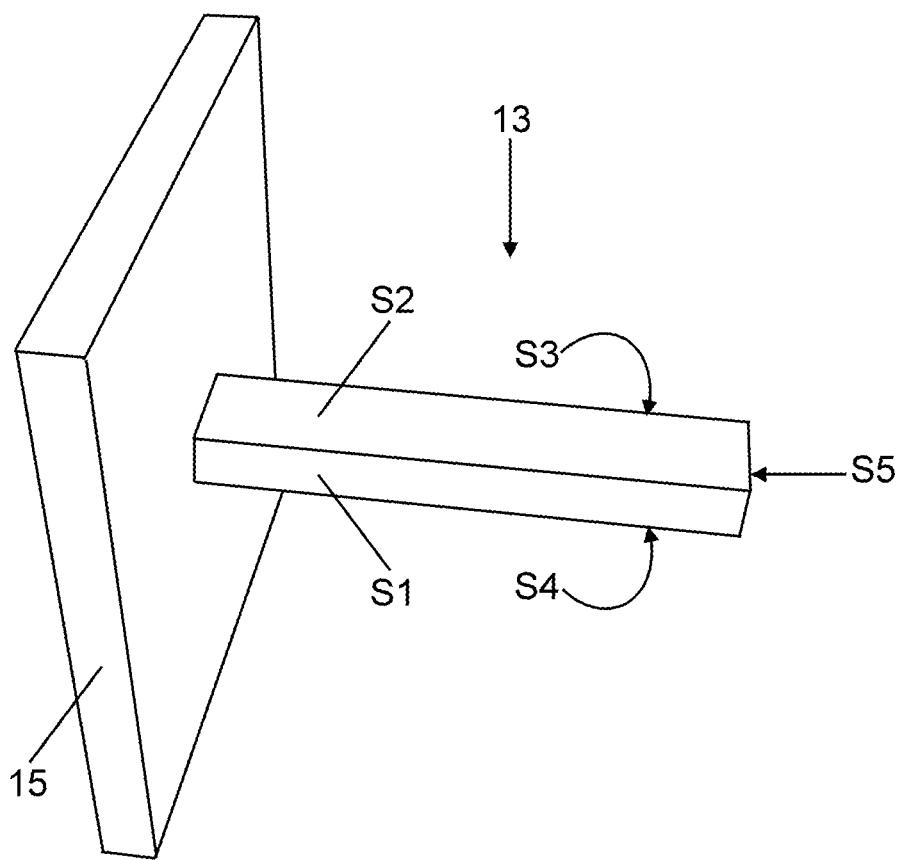
FIG. 2 is a perspective view of a stylized, exemplary, sulcus geometry used to illustrate representative effects of electrode location on the surface charge distribution of a sulcus's bounding surface.

FIG. 2 is a perspective view of a stylized, exemplary, sulcus geometry used to illustrate representative effects of electrode location on the surface charge distribution of a sulcus's bounding surface. Sulcus 13, which is filled with CSF, extends outward from a body 15, which is also filled with CSF. Body 15 can, for example, be a subarachnoid space or cavity of the brain or the spinal column, a ventricle, a larger portion of a sulcus from which a branch (the sulcus being simulated) extends, or the like. In this example, a conductivity value of 1.8 S/m was used for the CSF. See Baumann et al., "The Electrical Conductivity of Human Cerebrospinal Fluid at Body Temperature," *IEEE Trans Biomed Eng.* 1997 March; 44(3):220-3. This conductivity is substantially greater than that of the surrounding tissues and thus for the purposes of this analysis, the surrounding tissues are treated as having zero conductivity. Charge magnitudes will, in general, be reduced for finite conductivities of the surrounding tissues but the local configuration of the charge distribution will be largely unchanged because that configuration depends primarily on the local shapes of the surfaces of the sulcus and the body from which the sulcus extends.

The sulcus and the body form a continuous electrical medium and, as will be shown below, it is this continuum that produces the unique charge distributions associated with sulci. Thus, in FIG. 2, sulcus 13 represents a first anatomical structure filled with cerebrospinal fluid which projects from and is electrically continuous with a second anatomical structure which is also filled with cerebrospinal fluid.

To simplify the computations, sulcus 13 is rendered as a rectangular parallelepiped with an end surface S5 and side surfaces S1, S2, S3, and S4. Body 15 is also a rectangular parallelepiped. Rounding of the edges at which the sulcus meets the body and at which surfaces S1-S5 meet one another will diminish the sharpness of the transitions in charge/pixel values as one passes through an edge (see FIGS. 8 and 9), but the basic behavior will remain the same, e.g., the changes in polarity of the charge shown in FIGS. 8 and 9 as one transitions between the body and the sulcus will still occur. More generally, it will be understood that the geometry shown in FIG. 2 has been chosen so as not to obscure the central teachings of this disclosure and, in practice, the geometry will be more complex but the principles disclosed herein will continue to apply.

The computations of CSF charge distributions were performed using the $\Omega\delta \rightarrow 0$ processes of the '379 application with the following descretization of sulcus 13 and body 15:

(i) S1, S2, S3, and S4—11×44 flattened calculation cells each;
(ii) S5—11×11 flattened calculation cells;
(iii) four sides of body 15—11×55 flattened calculation cells each;
(iv) bottom of body 15—55×55 flattened calculation cells; and
(v) top of body 15—55×55 flattened calculation cells minus 11×11 cells at the center of the top of the body where the sulcus extends away from the body.

The total number of flattened calculation cells (each a square) was thus 10,406.

Figure 3:
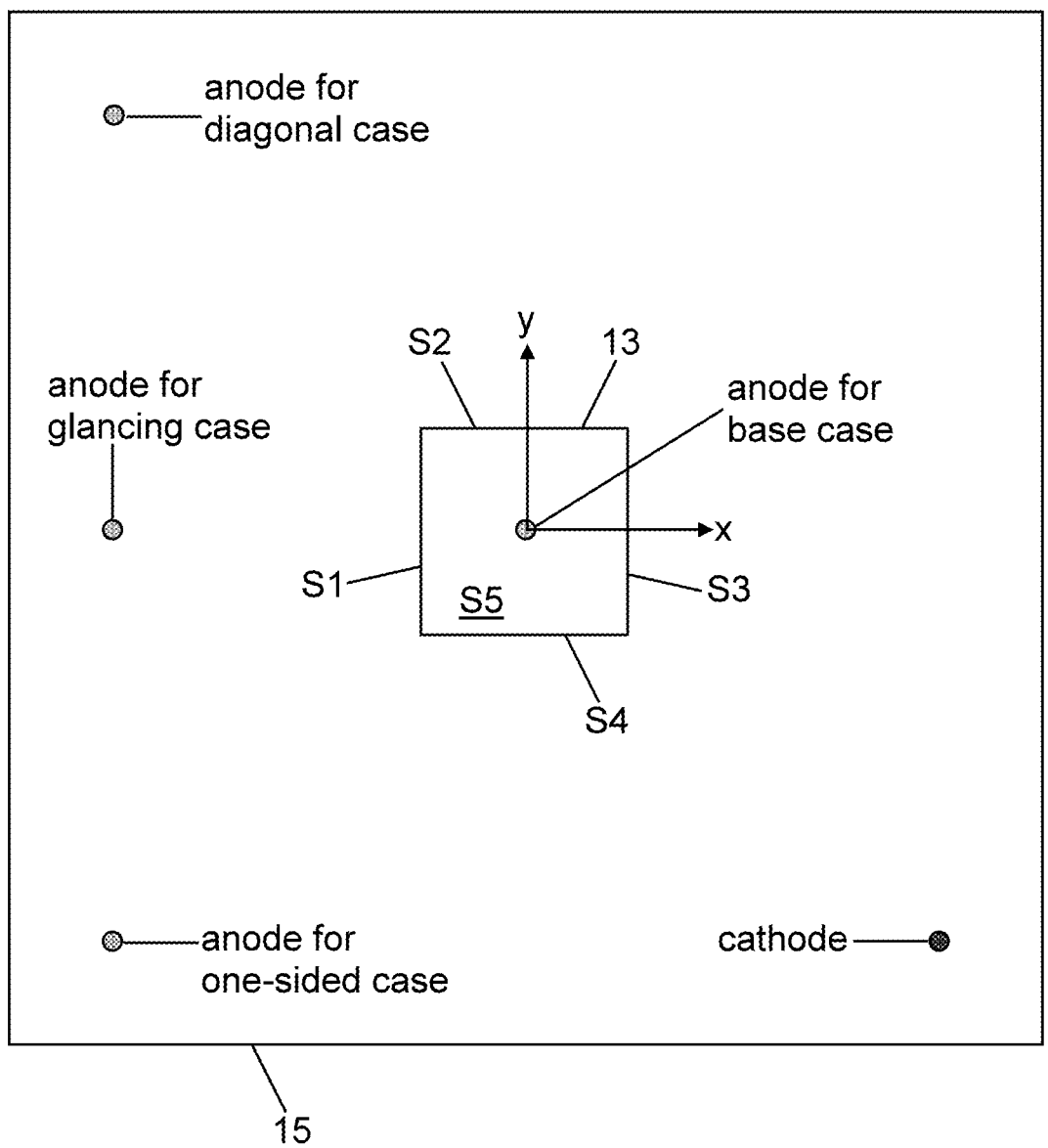
FIG. 3 is a plan view of the sulcus geometry of FIG. 2 illustrating a cathode location and four anode locations identified as the "base case," the "diagonal case," the "glancing case" and the "one-sided case." The bounding surface of the sulcus has five portions identified as S1, S2, S3, S4, and S5, where S1, S2, S3, S4 are side surfaces and S5 is an end surface.

The primary sources were represented by point sources located in the midplane between the top and bottom of the body. As illustrated in FIG. 3, to demonstrate various of the effects of electrode location on CSF charge distributions, four electrode configurations were used, designated as the "base case," the "diagonal case," the "glancing case," and the "one-sided case." The location of the cathode was held constant for the four cases. Specifically, the cathode was placed directly above the center of the flattened calculation cell that was 6 calculation cells up and 6 calculation cells in from the lower right hand corner of body 15 in FIG. 3.

For the base case, the anode was located at the center point of the body, i.e., it was directly above the center of the flattened calculation cell that was 28 calculation cells up and 28 calculation cells in from the lower right hand corner of the body in FIG. 3. Hence, for the base case, the anode was directly under the mouth of sulcus 13. For the remaining three cases, the anode was located 6 calculation cells in from the lower left hand corner of the body and 50, 28, and 6 calculation cells up from that corner for the diagonal, glancing, and one-sided cases, respectively. Hence, for the diagonal case, the straight line current path between the anode and the cathode was directly under the sulcus, while for glancing case, it was close to the lower left edge of the sulcus, and for the one-sided case, it was remote from the sulcus.

The four cases represent spatial relationships between electrode placements and a given sulcus which will frequently occur in practice. For a given electrode configuration, neighboring sulci to a given sulcus will in general have different spatial relationships to the electrodes than the given sulcus. For example, for any of the four anode locations of FIG. 3, a neighboring sulcus in the upper right hand corner of the figure would have a relationship to the electrodes like that of the one-sided case as opposed to any of the other three cases. The four cases of FIG. 3 are, of course, representative and not exhaustive of the types of spatial relationships that can exist between an anode/cathode pair and a given sulcus. The use of multiple anodes and/or multiple cathodes further expands the possible spatial relationships. In addition, CSF charge distributions on neighboring sulci interact with one another thus providing further richness in the types of charge distributions that can be achieved through the electrode placement and tissue stimulation process of the flowchart of FIG. 1. Further, while both the anode and cathode are located in CSF for the four cases illustrated in FIG. 3, in practice, some or all of the electrodes can be located in or on a non-CSF material, e.g., on a subject's skin.

Because both steady state CSF charge distributions and the time courses that lead to those steady state distributions are of interest, the $\Omega\delta \rightarrow 0$ processes of the '379 application were performed using Eqs. (27), (28), and (30) of that application, which for the conductivities and sources used in this example can be written:

$$q^f_A(t_{n+1}) = (1 - \Delta t \sigma_A / 2\varepsilon_0) q^f_A(t_n) - \Delta t \sigma_A / 4\pi\varepsilon_0 \Sigma_{i \neq A} q^f_i(t_n) \qquad \Omega_{a \leftarrow i} \tag{1}$$

$$q^f_B = 0 \tag{2}$$

$$q^f_{int}(t_{n+1}) = (1 - \Delta t \sigma_{int} / \varepsilon_0) q^f_{int}(t_n) + I^f_{int} \Delta t, \tag{3}$$

where, in the terminology of the '379 application, the int subscript represents an interior calculation cell, two of which were used in the calculations, i.e., one for the anode and the other for the cathode, and the A and B subscripts represent flattened calculation cells at the interface between the surrounding tissue and the sulcus/body, the A cell being on the higher conductivity side of the interface (the CSF side in these examples) and the B cell on the lower conductivity side (the non-conductor side in these examples). Because the B cells never contained charge, they were not explicitly included in the computations.

The summation in Eq. (1) includes the values of $q^f_{int}$ at the anode and the cathode at $t=t_n$, and, as in the '379 application, the $\Omega_{a \leftarrow i}$ values used in the summation are the solid angles as seen from the locations of the $q^f_i$'s of a face of the A cell whose charge is being computed. $\sigma_A$ and $\sigma_{int}$ in Eqs. (1) and (3) are each equal to the conductivity a of CSF. A $\Delta t$ of $\tau_{sigma}/10$ was used in the calculations, where $\tau_{sigma} = \varepsilon_0/\sigma$. $I^f_{int}$ in Eq. (3) was the constant current applied at the anode and the cathode, the current being positive at the anode and negative at the cathode. At $t_0$, the charge of all of the A cells was set equal to zero, the charge at the anode was set at $+V'_{int}\Delta t$, and that at the cathode at $-V'_{int}\Delta t$. Accordingly, the surface charge distributions of FIGS. 10A and 11A, which are for $t=0.1\tau_{sigma}$, are due solely to the initial anode and cathode charges, those being the only charges in the system during the transition from $t_0$ to $t_1$.

The magnitude of the steady state charge at the anode and cathode is given by (see Eq. (35) of the '379 application):

$$q'^{(ss)}_{int} = (\varepsilon_0/\sigma_{int})V'_{int} \qquad (4)$$

This value was used as the criterion for terminating the iterative process of Eqs. (1)-(3) used in calculating the charge distributions. Specifically, the iterative process was terminated when the magnitude of the change in the quantity of charge per iteration for each of the calculation cells dropped below $10^{-7} q'^{(ss)}_{int}$, which took ~1000 iterations, i.e., ~$100\tau_{sigma}$ since $\Delta t$ equaled $\tau_{sigma}/10$. The results discussed below are presented in terms of normalized rather than absolute values since Eqs. (1)-(4) vary linearly with $V'_{int}$ and thus any desired charge quantities can be achieved by adjusting $V'_{int}$ within efficacy and safety considerations. In addition, because the calculations were performed on a charge/pixel basis, the results are independent of the scale (dimensions) of the system, i.e., the results apply for sulcus/body combinations having the same or substantially the same configuration as that used in the computations irrespective of the size of the sulcus/body.

FIGS. 4-6 illustrate differences in steady state surface charge distributions resulting from changes in the locations of stimulating electrodes relative to the location of a sulcus. FIG. 4 plots normalized sums of the positive and negative charges on the S1, S2, S3, S4, and S5 portions of the bounding surface of sulcus 13. The surface charge on the S5 portion for the base case (see FIG. 4A) was used for the normalization. For reference, that surface charge was ~32% of $q'^{(ss)}_{int}$ of Eq. (4) above.

For further reference, the sums of the magnitudes of the positive and negative charges on S1, S2, S3, S4, and S5 for the base, diagonal, glancing, and one-sided cases were ~4.4 times, ~2.2 times, ~2.0 times, and ~1.5 times $q'^{(ss)}_{int}$, respectively, which illustrates how rapidly the surface charges can drop off as an electrode, in this case, an anode, moves out of direct alignment with a sulcus. The sums also illustrate how a sulcus can amplify the charge on an electrode, the sum of the magnitudes of the charges on the sulcus being greater than the magnitude of the charge on an electrode in all cases.

The amplification effect is particularly strong for the base case. In that case, all of the charges on the sulcus have the same sign as the charge on the electrode aligned with the mouth of the sulcus. As seen by other parts of the system, those charges cause the sulcus's effects to be more than four times greater than the effects of the electrode that was the primary source for the sulcus's charges, i.e., the electrode aligned with the sulcus's mouth. Moreover, the electrode plus sulcus combination is more than five times stronger than the electrode alone. Thus, when an electrode is aligned with the mouth of a sulcus, it can be expected to generate a stronger physiological response in the neural tissue being electrically stimulated than when the electrode is displaced from the mouth. This charge amplification effect is one of the effects that a practitioner can take into account in step 105 of FIG. 1 when evaluating candidate locations for stimulating electrodes.

Turning to FIGS. 5 and 6, these figures are polarity plots for portions S1, S2, S3, S4, and S5 of the sulcus's bounding surface as seen from the inside of the sulcus. Specifically, in FIG. 5, the sulcus has been cut along the edge between portions S1 and S4, and then folded outward to show the charge polarities of the portions. FIG. 6 shows the charge polarity of the S5 portion when looking outward from the interior of sulcus 13.

Beginning with the base case, its all positive polarity plots (FIGS. 5A and 6A) and all positive surface charge sums (FIG. 4A) can be readily understood using the pixel-as-a-sensor process discussed above, i.e., the process in which a surface charge distribution is analyzed/interpreted based on (i) positive (negative) surrounding charges on the higher conductivity side of a pixel seeking to induce positive (negative) surface charges at the pixel and (ii) positive (negative) charges on the lower conductivity side of a pixel seeking to induce negative (positive) surface charges at the pixel.

Starting with the effects of the primary charges at the electrodes, the positive anode which is aligned with the mouth of the sulcus is on the higher conductivity side of each pixel making up the bounding surface of sulcus 13. Accordingly, the positive anode seeks to induce a positive surface charge at each of those pixels. The negative cathode is on the lower conductivity side of the pixels of S3 and S4, and thus for these pixels, the cathode also seeks to induce a positive pixel charge. This combination of both the anode and the cathode seeking to induce positive surface charges results in the large positive sums for S3 and S4 shown in FIG. 4A.

Figure 4A:
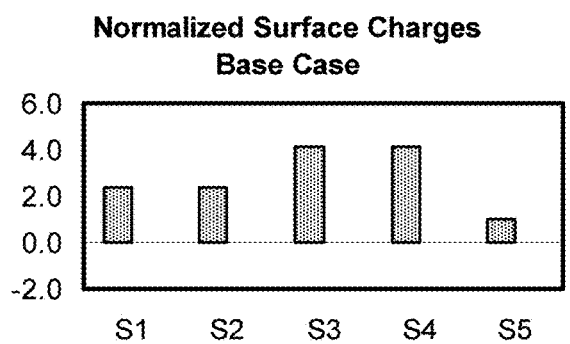
FIGS. 4A, 4B, 4C, and 4D are plots illustrating CSF charge distributions, specifically, the figures are plots showing normalized total positive and total negative surface charges at steady state for S1, S2, S3, S4, and S5 for, respectively, the base case, the diagonal case, the glancing case, and the one-sided case. The normalization is with respect to the S5 surface charge for the base case of FIG. 4A.

For S1 and S2, the cathode is on the higher conductivity side and thus it seeks to induce a negative surface charge at the pixels of these portions of the sulcus's bounding surface. However, the cathode is farther from the pixels than the anode and thus the pixels have smaller solid angles as seen from the cathode than from the anode. The magnitudes of the charges at the anode and the cathode being equal, the solid angle effect controls, thus making the resulting charge sums for S1 and S2 positive, but smaller than the sums for S3 and S4, as shown in FIG. 4A. Finally, with regard to S5, the cathode is again on the higher conductivity side of the pixels of this portion and thus seeks to induce a negative surface charge. However, as with S1 and S2, S5 is farther from the cathode than the anode and thus the net effect is positive surface charges for the pixels of S5 as a result of the solid angle effect.

It should be noted that the surface charges on each of S1, S2, S3, S4, and S5 are on the higher conductivity side of the other portions making up the bounding surface of the sulcus, i.e., the pixels of S1 are on the higher conductivity side of the pixels of each of S2, S3, S4, and S5, the pixels of S2 are on the higher conductivity side of the pixels of each of S1, S3, S4, and S5, and so forth. For the base case, all of the surface charges on the bounding surface of the sulcus due to the primary charges on the electrodes are positive. Accordingly, the surface charges on the sulcus start positive when the anode and cathode become active and thereafter stay positive through to the steady state since, as a consequence of being on the higher conductivity sides of one another, the positive surface charges on S1, S2, S3, S4, and S5 reinforce one another by seeking to induce positive surface charges on their neighbors. As we will see below, this is not always the case, e.g., for the diagonal, glancing, and one-sided cases, interaction between portions of the sulcus's bounding surface can override the effects of the charges on the electrodes at least locally. See the polarity plot for S5 for the diagonal case (FIG. 6B), the polarity plot for S1 for the glancing case (FIG. 5C), and FIGS. 10-12 for the one-sided case.

Turning to the diagonal case, as can be seen in FIG. 3, the anode and cathode lie on opposite sides of a symmetry plane through the edges of the S1/S4 and S2/S3 intersections. This symmetry manifests itself in the symmetry (or, more precisely, the anti-symmetry) of the polarity plot of FIG. 5B, where S1 and S2 nearest the anode have negative surface charges and S3 and S4 nearest the cathode have positive surface charges. The anti-symmetry can also be seen in FIG. 4B, where the sums of the surface charges on S1 and S2 are equal and opposite to the sums on S3 and S4.

The pixel-as-a-sensor process readily leads to the negative surface charges on S1 and S2 and the positive surface charges on S3 and S4. Starting with S1 and S2, the anode is behind and the cathode is in front of the higher conductivity sides of the pixels of these portions of the sulcus's surface, so both primary sources seek to induce the negative surface charges seen on S1 and S2. Conversely, for S3 and S4, the anode is in front of the higher conductivity sides of the pixels of these portions of the sulcus's bounding surface and the cathode is behind the higher conductivity sides, so that the surface charges are positive for S3 and S4.

Figure 6A:
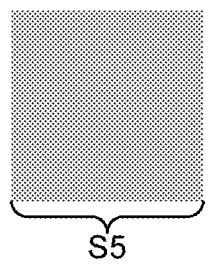
FIGS. 6A, 6B, 6C, and 6D are plots illustrating CSF charge distributions, specifically, the figures are polarity plots at steady state of the S5 surface charges for, respectively, the base case, the diagonal case, the glancing case, and the one-sided case.
Figure 6B:
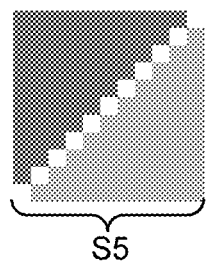

As shown in FIG. 6B, the surface charges on S5 also exhibit anti-symmetry, but the anti-symmetry is opposite to that which the charges on the anode and cathode would induce. Thus, both the anode and the cathode are on the higher conductivity side of the pixels of S5. Consequently, the charges on the anode seek to induce positive surface charges on S5 and the charges on the cathode seek to induce negative surface charges. Because the anode is nearer to the pixels closest to S1 and S2 and the cathode is nearer to the pixels closest to S3 and S4, if the only surrounding charges acting on the pixels of S5 were the charges of the anode and the cathode, the polarity would be positive near S1 and S2, and negative near S3 and S4. However, as can be seen in FIG. 6B, just the opposite is found.

Figure 4B:
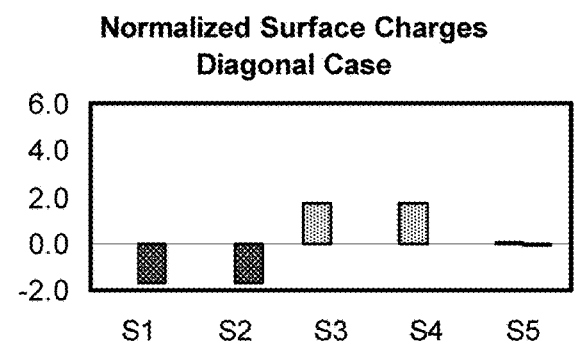

This reversal occurs because of the strong negative charges on S1 and S2 and the strong positive charges on S3 and S4 (see FIG. 4B). These charges are on the higher conductivity side of the pixels of S5 and thus the negative charges on S1 and S2 seek to induce negative surface charges on S5 and the positive charges on S3 and S4 seek to induce positive surface charges on S5. When the relative proximities and orientations of the pixels of S5 to (i) the charges on the anode and cathode and (ii) the charges on S1, S2, S3, and S4 are taken into account, the charges on S1, S2, S3, and S4 are both nearer to the S5 pixels and more head-on to those pixels, i.e., they make smaller angles with the normals to the S5 pixels, both of which lead to larger solid angles for the S1-S4 charges than the primary charges on the electrodes. Hence, the charges on the S1-S4 portions dominate. The final surface charge distribution on S5 then depends on the relative proximities to individual S5 pixels of (i) positive charges on S1 and S2 and (ii) negative charges on S3 and S4. The result of this interaction is the polarity plot of FIG. 6B with negative surface charges for the pixels closer to S1 and S2, positive surface charges for the pixels closer to S3 and S4, and no charges along the diagonal, where the effects of the positive and negative charges on S1/S2 and S3/S4 cancel out, as do the effects of the positive and negative charges on the anode and cathode.

Figure 6C:
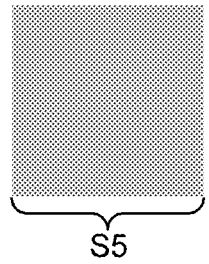
Figure 6D:
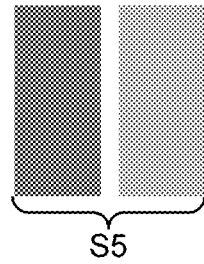

This interaction between surface charges on different portions of the bounding surface of a sulcus is further illustrated in the polarity plot of FIG. 5C for the glancing case. Compared to the polarity plot of FIG. 5B for the diagonal case, we see in FIG. 5C that the new position of the anode causes positive polarity to invade parts of S1 and S2, and negative polarity to appear at an edge of S4 (specifically, the edge nearest the lower left hand corner of sulcus 13 in FIG. 3). It also causes the polarity of S5 to become all positive (FIG. 6C). Only the polarity of S3 remains the same, i.e., all positive.

Figure 4C:
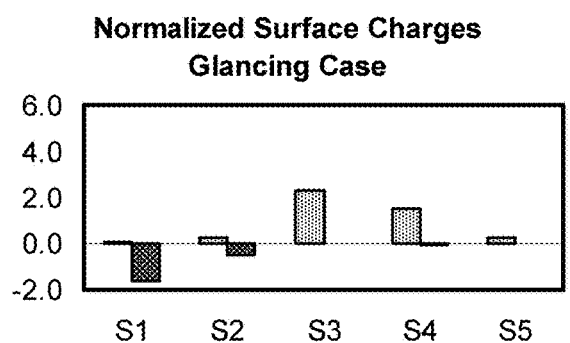
Figure 4D:
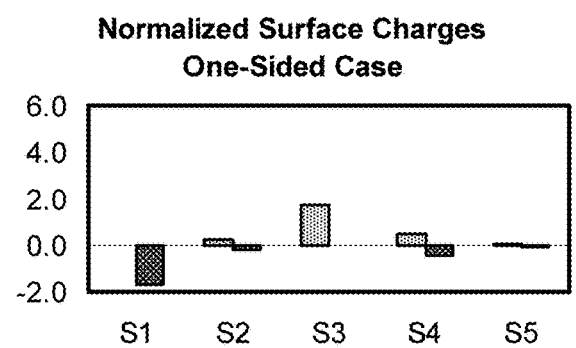

Again, the pixel-as-a-sensor process explains these changes. Beginning with S3, as in the diagonal case, both the positive charges on the anode and the negative charges on the cathode seek to induce positive surface charges on S3, the anode being on the higher conductivity side of the S3 pixels and the cathode being on the lower conductivity side. Moreover, the anode is now head-on to S3 so that its effects are felt more strongly. Specifically, the lines of sight from the anode to the pixels of S3 with the anode in its glancing-case position are closer to the normals to the S3 pixels than they are when the anode is at its diagonal-case position. This makes the solid angles of the S3 pixels as seen from the anode larger and the effects of the anode's charges stronger. This effect can be seen in FIGS. 4B and 4C where the sum of the surface charges on S3 for the diagonal case (FIG. 4B) is smaller than the sum of the surface charges on S3 for the glancing case (FIG. 4C).

Turning next to S5, its all positive polarity for the glancing case can be understood in terms of proximity and lines of sight. Specifically, the effects of the anode on S5 for the glancing case are stronger than the effects of the cathode both because the anode is closer to S5 than the cathode and because the lines of sight from the anode to the S5 pixels are closer to the normals to the pixels than the lines of sight from the cathode. Also, the effects on S5 of the charges of S1, S2, S3, and S4 tend to be dominated by the strong positive charge of S3 which reinforces (amplifies) the ability of the anode to induce positive surface charges on S5.

The polarity plots for S1 and S4 for the glancing case can be viewed as basically the same as those of the diagonal case with modifications primarily due to (i) the positive charges on S5 in the case of S1 and (ii) the negative charges on S1 in the case of S4. Thus, as in the diagonal case, the anode and cathode both seek to make S1 negative and S4 positive, the positive charges of the anode being on the lower conductivity side and the negative charges of the cathode being on the higher conductivity side of S1 and vice versa for S4. The higher conductivity sides of the pixels of S1, however, also see the positive charges of S5 and these charges seek to induce positive surface charges on S1. This effect is strongest for the part of S1 closest to S5 and thus in FIG. 5C we see positive polarities near the top of S1 in that figure. For S4, it is the negative charges of S1 that seek to induce negative surface charges on S4. For most of S4, the effects of these S1 negative charges are not strong enough to change the polarity from positive to negative, but right at the junction of S1 and S4 a small number of pixels make the switch.

Like the diagonal case, the one-sided case has a plane of symmetry, in this case along the y-axis of FIG. 3. As in the diagonal and glancing cases, the anode and cathode cooperate at S1 and S3 producing surface charges which are all negative and all positive, respectively (see FIG. 4D and FIG. 5D). The anode and cathode, as well as the charges on S1 and S3, compete for S2 and S4. For S4, the final polarities are as would be expected from the locations of the anode and cathode, i.e., negative for the parts of S4 nearest the anode and positive for the parts nearest the cathode since both the anode and the cathode are on the lower conductivity sides of the pixels of S4. However, as will be discussed more fully below in connection with FIG. 10, for S2, the charges on S1 and S3 come to dominate with the part of S2 nearest the anode ending up with a negative polarity rather than a positive polarity and the part nearest the cathode ending up with a positive polarity rather than a negative polarity even though both the anode and the cathode are on the higher conductivity sides of the pixels of S2 and thus are seeking to induce positive and negative charges, respectively, at the S2 pixels. This same domination by the S1 and S3 charges occurs for the S5 pixels as shown in FIG. 11, also discussed below.

In addition to the primary charges at the electrodes and the mutual interaction between the charges on the various portions of the bounding surface of the sulcus, the CSF charge distribution is also influenced by the charges on the surface of body 15 from which sulcus 13 emanates. In general terms, the effects of these body-surface charges reinforce the effects of the primary charges on the electrodes, the portions of the body surface near the anode having positive surface charges and those near the cathode having negative surface charges for electrodes within the CSF of body 15.

FIG. 8 and FIG. 9 illustrate another consequence of treating pixels as sensors of the charges in their surroundings. These figures plot normalized charge/pixel values as a function of pixel number for the traces shown in FIG. 7, where the portion of the trace identified by the reference number 17 in FIG. 7 represents pixels with negative pixel numbers in FIGS. 8 and 9 and the portion identified by the reference number 19 represents pixels with positive pixel numbers. The traces in FIG. 8 are along the x-axis in FIG. 3 and move across S5 and then along S1 or along S3 for negative/positive pixel numbers, respectively, and then out onto the top surface of body 15; the traces in FIG. 9 are along the y-axis in FIG. 3 and move across S5 and then along S4 or along S2 for negative/positive pixel numbers, respectively, and then out onto the top surface of body 15. The normalization is relative to the charge/pixel for the "0" pixel for the base case. For reference, that charge is ~0.2% of $q'^{(ss)}_{int}$ of Eq. (4) above.

The most prominent features of FIGS. 8 and 9 are the sharp changes in polarity that occur at each transition from sulcus 13 to body 15. The pixel-as-a-sensor process readily explains this sharp transition. Consider two pixels, one of which belongs to body 15 near to a transition (the first pixel) and the other of which belongs to the sulcus also near the transition (the second pixel). Because of the intervening corner between the pixels, the charge of each of these two pixels is on the lower conductivity side of the other pixel. Hence, if the charge in the first pixel is positive, it will seek to induce a negative surface charge in the second pixel. A negative surface charge in the second pixel will, in turn, seek to induce a positive surface charge in the first pixel, which will then seek to induce an even more negative charge in the second pixel, and so on. The two pixels will thus feed back on one another leading to the sharp changes in polarity seen at the transitions in FIGS. 8 and 9. In anatomical sulci, the sharpness of the change in polarity will be muted because instead of a sharp corner, the transition will be a smooth curve, but the feedback relationship will still exist between pixels on the sulcus and pixels on the body near to the transition and thus, subject to the effects of neighboring sulci and the like, the sign of the surface charge will change as one moves along a surface which enters the mouth of a sulcus.

Figure 8A:
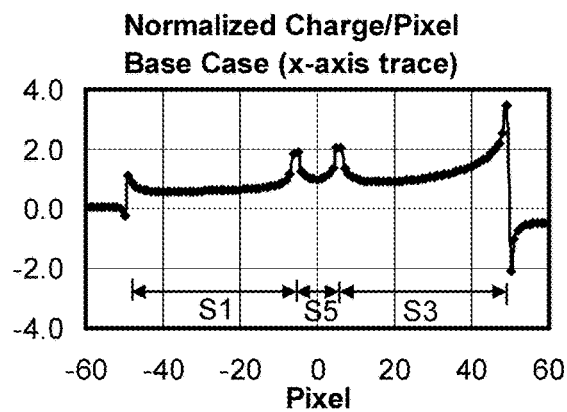
FIGS. 8A, 8B, 8C, and 8D are plots illustrating CSF charge distributions, specifically, the figures are x-axis trace plots at steady state for, respectively, the base case, the diagonal case, the glancing case, and the one-sided case. The values plotted in these figures and those of FIG. 9 are normalized to the charge/pixel value of the "0" pixel of the base case of FIG. 8A or, equivalently, the base case of FIG. 9A, which has the same value for the "0" pixel.
Figure 8B:
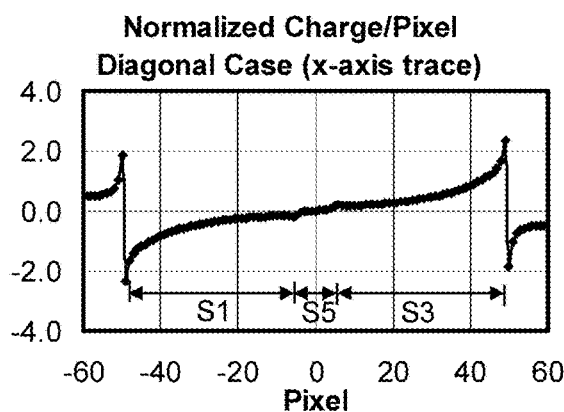
Figure 8C:
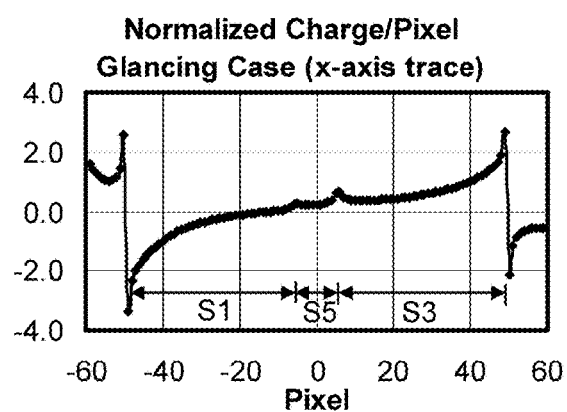
Figure 8D:
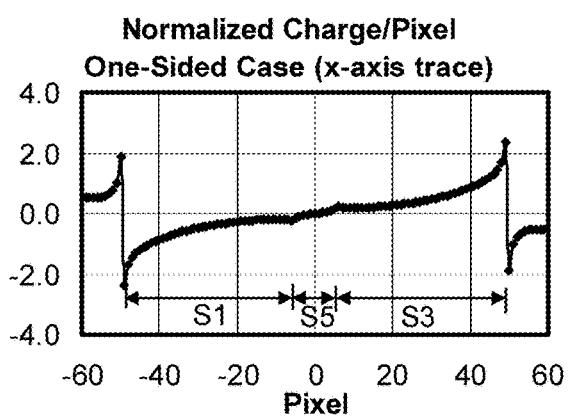
Figure 9A:
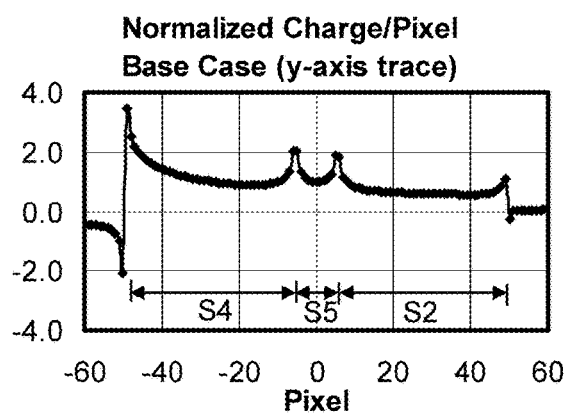
FIGS. 9A, 9B, 9C, and 9D are plots illustrating CSF charge distributions, specifically, the figures are y-axis trace plots at steady state for, respectively, the base case, the diagonal case, the glancing case, and the one-sided case.
Figure 9B:
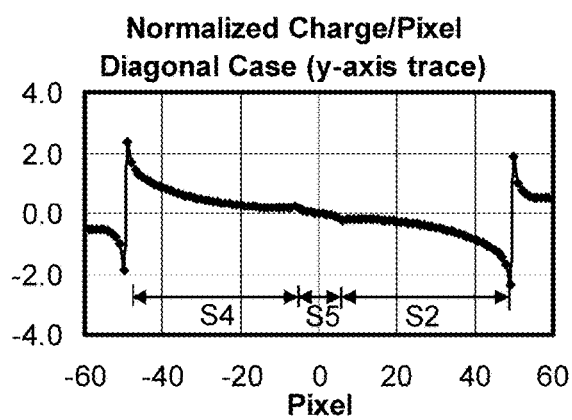
Figure 9C:
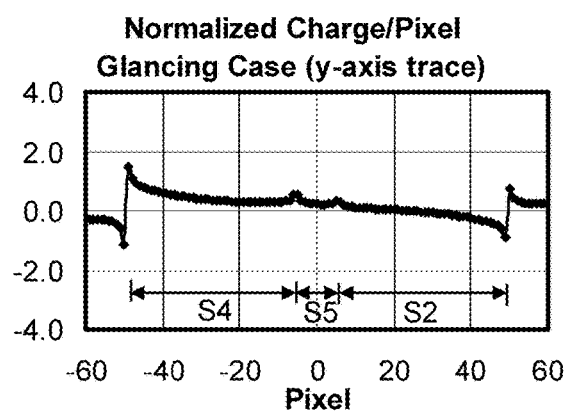
Figure 9D:
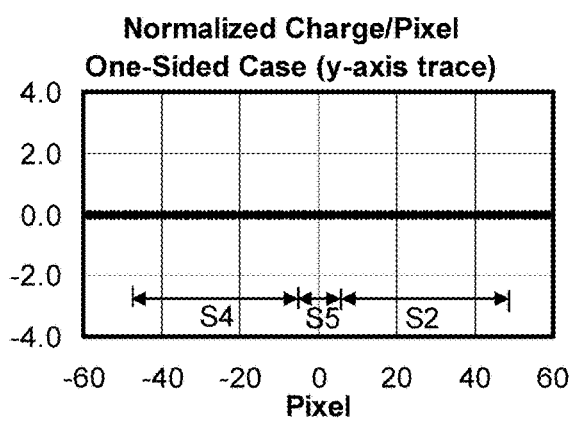

The transition between S5 and any of S1, S2, S3, and S4 also exhibits feedback as can be seen most strongly in FIGS. 8A and 9A. Again consider two pixels, a first pixel on S5 and a second pixel on S1, S2, S3, or S4, both near the transition. Because of the intervening corner between the pixels, the charge of each of these two pixels is on the higher conductivity side of the other pixel. Hence, if the charge in the first pixel is positive, it will seek to induce a positive surface charge in the second pixel. A positive surface charge in the second pixel will, in turn, seek to induce an even more positive surface charge in the first pixel, which will then seek to induce a still more positive charge in the second pixel, and so on. The magnitude of the charges on S5 and the parts of S1, S2, S3, and S4 near S5 being smaller than the magnitudes of the charges on body 15 and the parts of S1, S2, S3, and S4 near the body, the effect of the S5 to S1, S2, S3, or S4 transition is smaller than the effect of the S1, S2, S3, or S4 transition to body 15 in FIGS. 8 and 9. However, in both cases, the existence of this feedback mechanism at transitions provides insight into the mechanisms at work in modifying of neural activity through electrical stimulation. The insight comes from CSF charge distributions, not from potential, electrical field, or current density distributions.

FIGS. 10-12 use the one-sided case to illustrate how the charges on the bounding surface of a sulcus can interact with each other and with the charges on the electrodes over time to produce a final CSF charge distribution different from that which the electrodes alone would produce. In particular, FIG. 10 shows how the effects of the growing negative surface charge on S1 and the growing positive surface charge on S3 (both due at least initially to the charges on the anode and cathode) invade S2 and cause it to change from a positive-zero-negative polarity pattern (left to right in FIG. 10A) due only to the charges on the electrodes to a negative-zero-positive polarity pattern (left to right in FIG. 10H and FIG. 5D) at steady state. The same switch from a positive-zero-negative polarity pattern to a negative-zero-positive polarity pattern occurs for S5 as shown in FIG. 11.

Figure 12A:
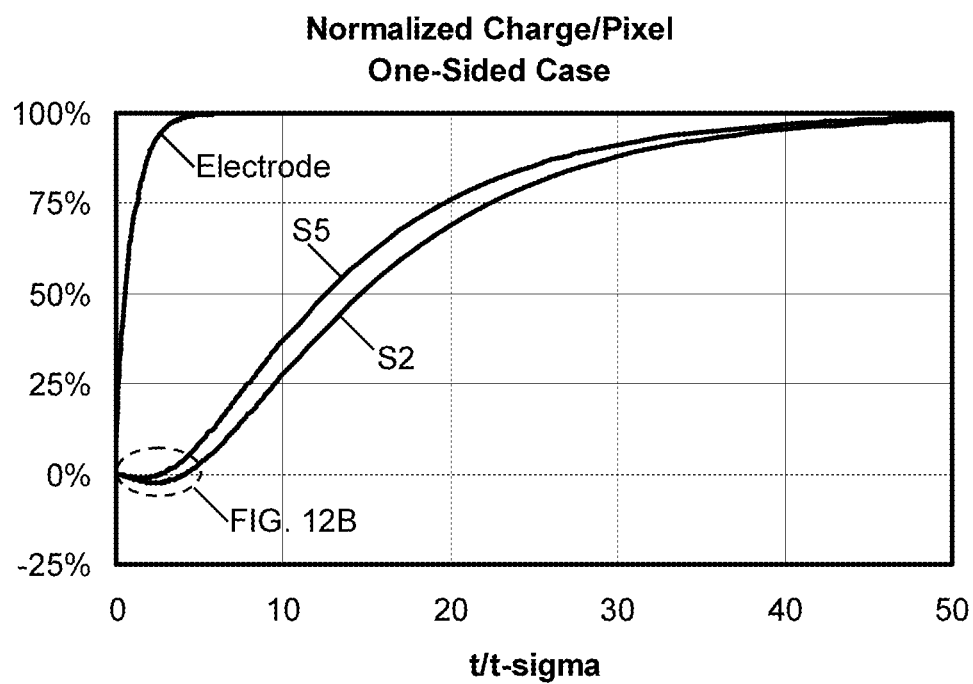
FIG. 12A is a plot illustrating CSF charge distributions, specifically, the figure plots normalized charge/pixel as a function of time for the S2 and S5 pixels marked by asterisks in FIGS. 10 and 11, respectively. The plot also shows the growth of charge at the system's electrodes, the same time course occurring at both the anode and the cathode. The axis label "t-sigma" in this figure and in FIG. 12B is the same as the label "$\tau_{sigma}$" in FIGS. 10 and 11. The normalization for the S2 and S5 curves in FIGS. 12A and 12B is to their respective steady state values; the normalization for the electrode in FIG. 12A is to the steady state charge at the electrode.
Figure 12B:
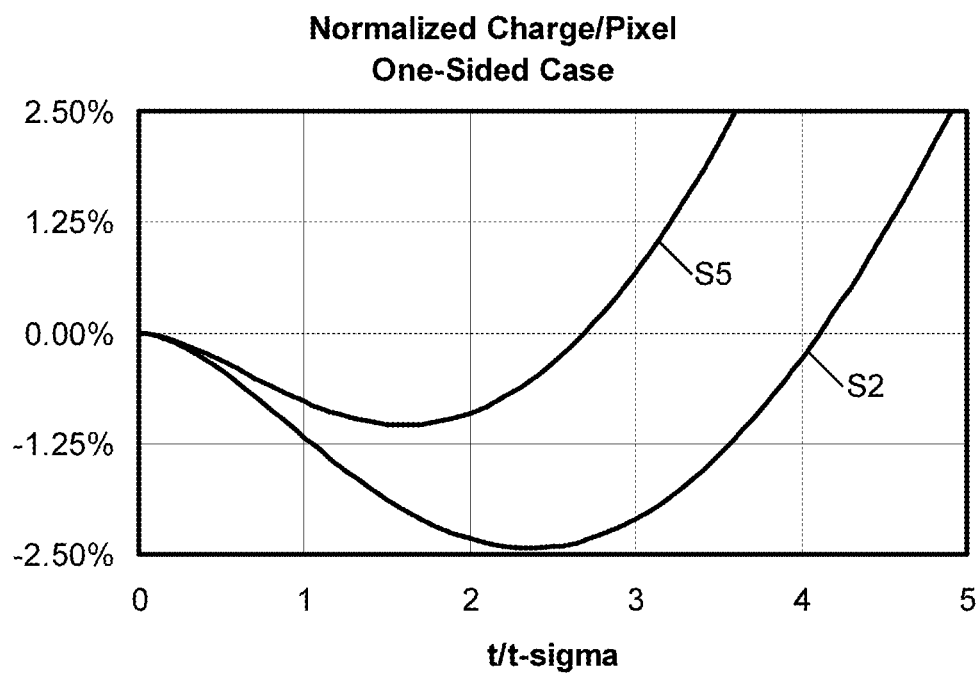
FIG. 12B is an expanded version of the time course of the charges at the S2 and S5 asterisk pixels of FIGS. 10 and 11 for t=0 through t=5.0 $\tau_{sigma}$ (see the dashed oval in FIG. 12A).

The time course of this switch in polarity pattern is further illustrated in FIG. 12 for the pixels identified by asterisks in FIGS. 10 and 11. These plots are normalized to the pixel's charge at steady state which is negative in both cases. Hence, the switch from negative to positive percentages in FIGS. 12A and 12B are changes from positive charges to negative charges at the pixels. For reference, FIG. 12A also includes a normalized time course for the growth in charge at the electrodes.

Figure 10A:
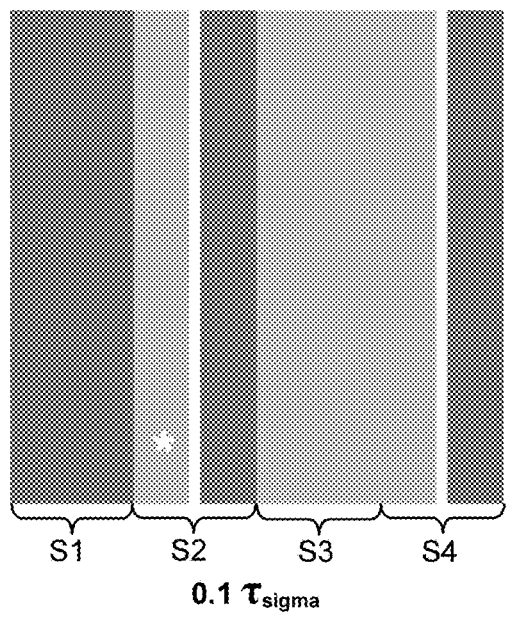
FIGS. 10A, 10B, 10C, 10D, 10E, 10F, 10G, and 10H are plots illustrating CSF charge distributions, specifically, the figures are polarity plots of the S1, S2, S3, and S4 surface charges for the one-sided case as a function of time.
Figure 10B:
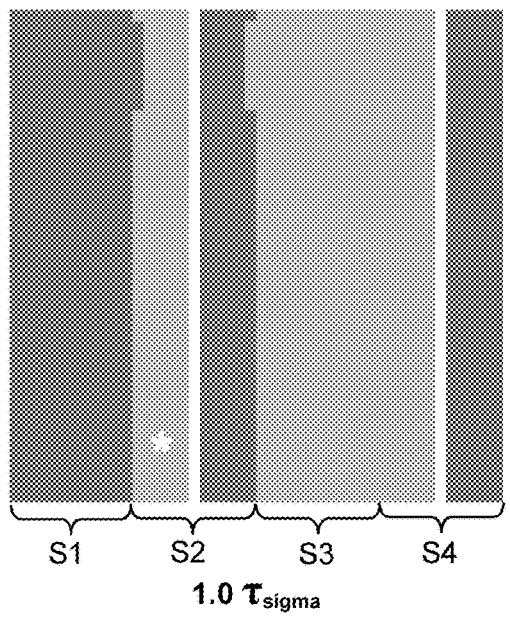
Figure 10C:
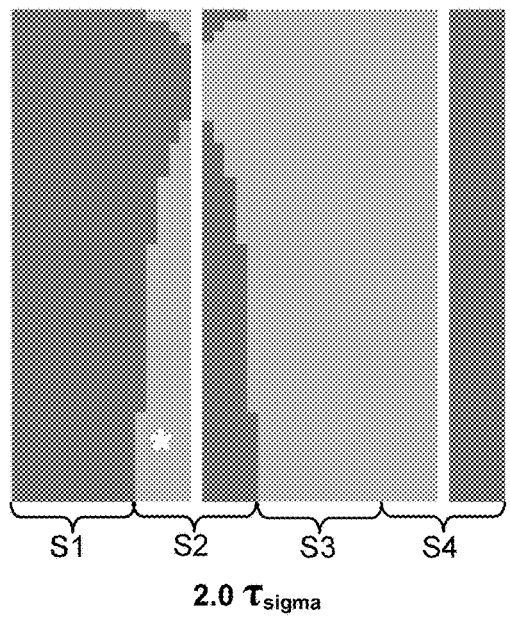
Figure 10D:
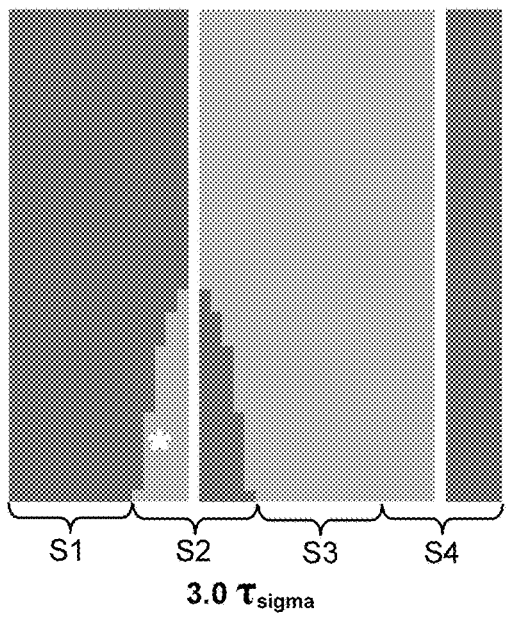
Figure 10E:
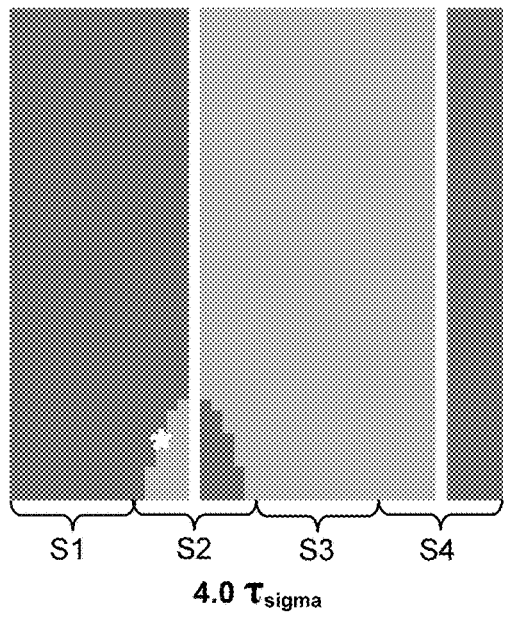
Figure 10F:
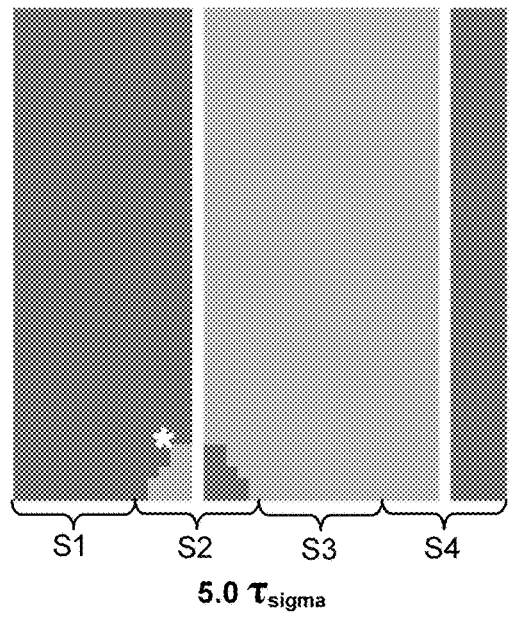
Figure 10G:
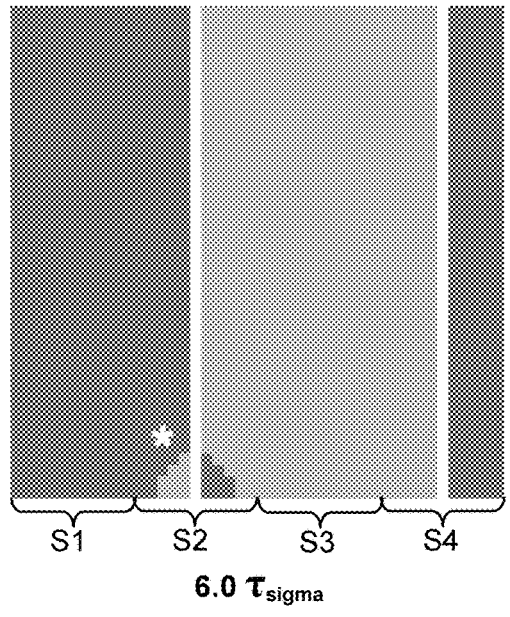
Figure 10H:
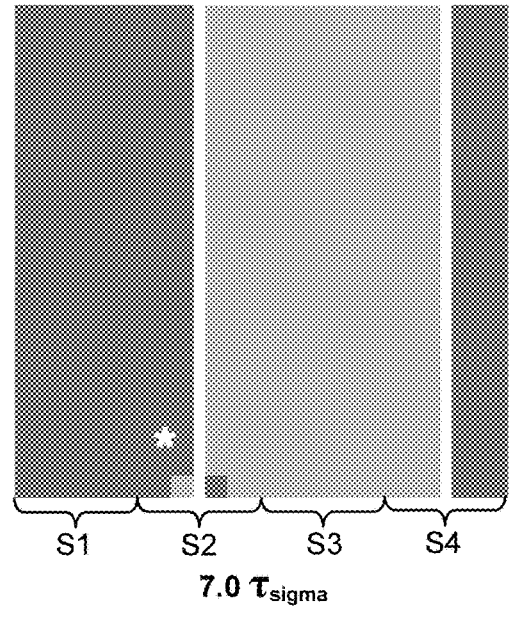
Figure 11A:
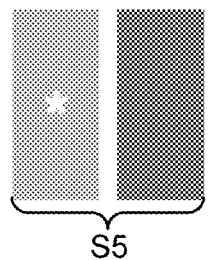
FIGS. 11A, 11B, 11C, 11D, and 11E are plots illustrating CSF charge distributions, specifically, the figures are polarity plots for the S5 surface charges for the one-sided case as a function of time.
Figure 11B:
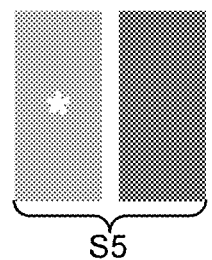
Figure 11C:
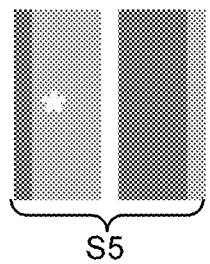
Figure 11D:
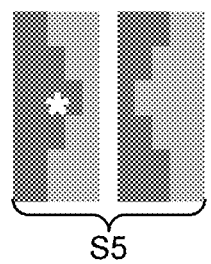
Figure 11E:
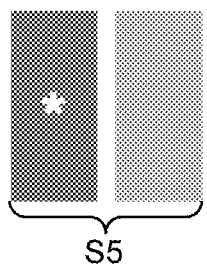

From FIG. 12B, we see that the charge at the S2 asterisk pixel turns negative (i.e., acquires a positive percentage value in this figure) between $4\tau_{sigma}$ and $5\tau_{sigma}$, which correspond to FIG. 10E and FIG. 10F, respectively. We also see that the S5 asterisk pixel turns negative sooner, i.e., between $2\tau_{sigma}$ and $3\tau_{sigma}$, which correspond to FIG. 11C and FIG. 11D, respectively. As can be seen in FIG. 12A, the faster time course for the S5 asterisk pixel compared to the S2 asterisk pixel continues throughout the growth of the negative charge at these pixels.

The results of FIGS. 4-6 and 8-12, as well as those of FIGS. 15-25 to be discussed below, are illustrative, but not limiting, examples of the use of CSF charge distributions to evaluate candidate electrode locations to be used to modify neural activity. Among other things, these figures illustrate how the pixel-as-a-sensor process can be used to evaluate charge distributions and predict how they will change with changes in electrode locations. Compared to potentials, electric fields, and current densities, this ability to analyze/interpret the underpinnings of surface charge distributions makes such distributions a much preferred way of selecting electrode locations for modifying the activity of neural tissues through electrical stimulation.

Example 2

Figure 13:
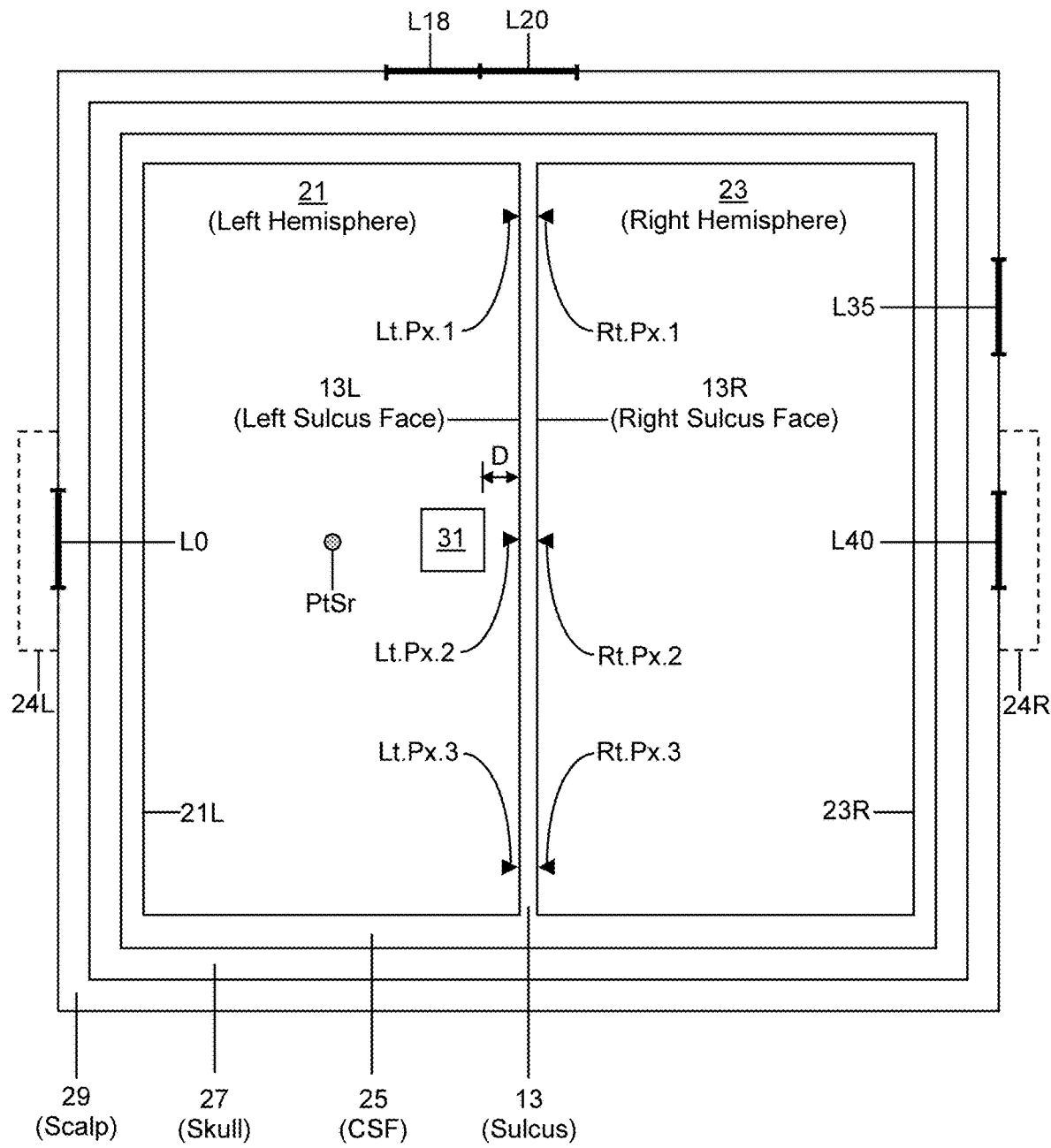
FIG. 13 is a cross-section of a stylized, exemplary, human brain that includes sulcus 13. Along with FIGS. 15-25, the figure illustrates representative effects of electrode location on the surface charge distribution of a sulcus's bounding surface.

FIG. 13 is another stylized, exemplary, sulcus geometry used to illustrate representative effects of electrode location on the surface charge distribution of a sulcus's bounding surface, as well as the pixel-as-a-sensor process.

Sulcus 13 in this case is located between two rectangular parallelepipeds 21 and 23 having the conductivity of brain tissue. Surrounding the rectangular parallelepipeds is a layer 25 having the conductivity of CSF, which, in turn, is surrounded by a layer 27 having the conductivity of the skull and a layer 29 having the conductivity of the scalp.

The dimensions and conductivities of the sulcus, rectangular parallelepipeds, and the CSF, skull, and scalp layers were chosen to be like those of the human head. Specifically, the dimensions and conductivities were based on those given in Datta et al., "Transcranial current stimulation focality using disc and ring electrode configurations: FEM analysis," *J. Neural Eng.* 2008, 5:163-174, for a four concentric sphere model of the human head. See also Datta et al., "Gyriprecise head model of transcranial direct current stimulation: Improved spatial focality using a ring electrode versus conventional rectangular pad," *Brain Stimulation*, 2009, 2:201-207e1, which used the same conductivity values for a MRI-based analysis. A rectangular geometry, rather than a spherical geometry, was used to facilitate the presentation of surface charge distributions on the sulcus's bounding surface (see FIGS. 15-17 and 19-23 below).

The cross-section of FIG. 13 can be considered an axial section as seen from below so that rectangular parallelepiped 21 approximates the brain's left hemisphere and rectangular parallelepiped 23, the right, with sulcus 13 approximating the brain's longitudinal fissure. In view of the symmetry of the stylized system of this example, the cross-section of FIG. 13 can also be considered a coronal section seen from behind so that rectangular parallelepiped 21, rectangular parallelepiped 23, and sulcus 13 again approximate the left hemisphere, the right hemisphere, and longitudinal fissure, respectively. (Note that for the convention typically used in MRI images, the locations of the left and right hemispheres in the cross-sections would be reversed.) For purposes of the following discussion, the coronal-section-from-behind orientation for the cross-section will be assumed, with dashed rectangles 24L and 24R at the left and the right of the cross-section representing the subject's left and right ears, respectively, the subject's nose, which is behind the plane of the figure, not being intersected by the section for this orientation.

Charge distributions were computed using the $\Omega\delta \to 0$ processes of the '379 application. A total of 8,976 pixels (flattened (2D) calculation cells), each a square, was used to represent the system as follows. The interface between the surrounding air and scalp layer 29 was represented by a total of 2,400 pixels (6×(20×20)), each pixel having an edge length of 7.50 mm and each of the six panels making up the interface being a 150 mm×150 mm square; the interface between scalp layer 29 and skull layer 27 was represented by a total of 1,944 pixels (6×(18×18)), each pixel having an edge length of 7.78 mm and each of the six panels making up the interface being a 140 mm×140 mm square; and the interface between skull layer 27 and CSF layer 25 was represented by a total of 1,944 pixels (6×(18×18)), each pixel having an edge length of 7.22 mm and each of the six panels making up the interface being a 130 mm×130 mm square. The thicknesses of scalp layer 29 and skull layer 27 were each 5 mm.

The right panel of left rectangular parallelepiped 21 and the left panel of right rectangular parallelepiped 23 formed the bounding surface (13L,13R) of sulcus 13, whose thickness was set at 2 mm. Each of these panels used 576 pixels (24×24), each pixel having an edge length of 5 mm so that each of the CSF/brain interfaces of the sulcus was a 120 mm×120 mm square.

The remaining panels of rectangular parallelepipeds 21 and 23 used pixels having an edge length of 7.50 mm. Left panel 21L and right panel 23R of the parallelepipeds were 120 mm×120 mm squares each composed of 256 pixels (16×16), while the remaining four panels of the parallelepipeds were 60 mm×120 mm rectangles, each composed of 128 pixels (8×16). CSF layer 25 was thus 4 mm thick at panels 21L and 23R and 5 mm thick at the remaining four panels of the rectangular parallelepipeds.

Electrode locations in FIG. 13 and in FIGS. 15-23 are designated in terms of perimeter distances along the scalp measured from the center of the left hand panel of the scalp/air interface (the "origin"). The electrode locations are expressed in terms of the edge length of the pixels of that interface which, as discussed above, for these simulations was 7.50 mm. Hence, an anode at the center of the left hand panel of the scalp/air interface is at "L0", a cathode at the center of the right hand panel is at "L40" (300 mm from the origin), and an electrode centered over sulcus 13 is at "L20" (150 mm from the origin).

Figure 14:
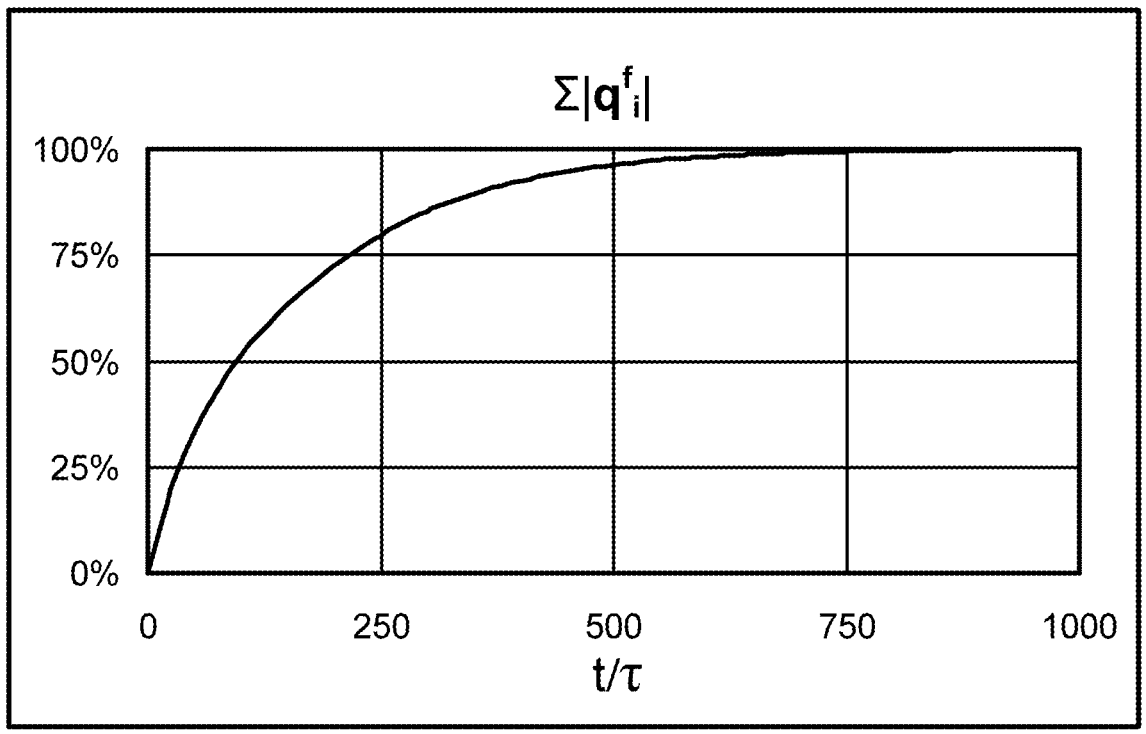
FIG. 14 is a plot illustrating the convergence of the $\Omega\delta\rightarrow0$ processes of the '379 application for the geometry of FIG. 13.

In accordance with Datta et al., 2008, supra, and Datta et al., 2009, supra, the conductivities ($\sigma$'s) of the scalp, skull, CSF, and brain were 0.465, 0.010, 1.650, and 0.200 S/m, respectively, corresponding to time constants ($\tau = \varepsilon_0/\sigma$) of $1.90 \times 10^{-11}$, $8.85 \times 10^{-10}$, $5.37 \times 10^{-12}$, and $4.43 \times 10^{-11}$ seconds. A time step of $5.37 \times 10^{-13}$ seconds was used in this example and in Example 3, except for the right most data point in FIG. 25 where a smaller time step of $1.07 \times 10^{-13}$ seconds was used in view of the 100.0 S/m conductivity of region 31 used for that data point, which corresponds to a time constant of $8.85 \times 10^{-14}$. FIG. 14 shows the time course of the sum of the magnitudes of the charges at the system's 8,976 pixels ($\Sigma |q^f_i|$) as a function of the CSF time constant ($5.37 \times 10^{-12}$ seconds) for the case of an anode at L0 in FIG. 13 and a cathode at L40. To ensure convergence, 1,000 CSF time constants were used for all of the calculations of this example and Example 3, although as shown in FIG. 14, less iterations could have been used.

As a point of interest, for a current flow of 1.0 milliamp between the anode at L0 and the cathode at L40, $\Sigma |q^f_i|$ is $2.00 \times 10^7$ elementary charges or 3.20 picocoulombs. This value is of the same order of magnitude as the sum of the magnitudes of the charges on the two sides of a biological membrane for a resting potential on the order of 100 mV. See Klee, M. M., "Biology's built-in Faraday cages," *Am. J. Phys.*, vol. 82, no. 6, pp. 451-459, n7. The number of coulombs passing through the system per second corresponding to 1.0 milliamp of current is 1.0 millicoulomb. Thus, charge accumulations in the picocoulomb range generate electric fields that are sufficiently strong (in the mV/mm range) to guide millicoulombs of charge from anode to cathode each second. While the sum of the magnitudes of the charges is in the picocoulomb range, the sum of the charges taking into account their signs although not exactly zero because of round-off errors is a tiny fraction of the sum of the magnitudes since the $\Omega\delta \to 0$ processes of the '379 application accurately conserve charge, e.g., the maximum residue charge throughout the time course of FIG. 14 had a magnitude of $\sim 6 \times 10^{-6}$ elementary charges corresponding to a charge imbalance on the order of less than one part in $10^{13}$.

As discussed in the '379 application, free charges only accumulate on the higher conductivity side of an interface between two conductors assuming, as is the case here, that current is not introduced at the interface's lower conductivity side and that there are no initial charges on that side. Thus, charges only accumulate on the inner and outer surfaces of scalp layer 29, the inner and outer surfaces of CSF layer 25, and the left and right faces of sulcus 13, but not on the inner and outer surfaces of skull layer 27 or the outer surfaces of brain tissue 21 and 23 since the skull and brain tissue have lower conductivities than their surroundings. Charges also do not accumulate on the air side of the air/scalp interface.

Because charges only accumulate on the higher conductivity side of a conductivity interface (the A cell side of the interface in the nomenclature of the '379 application), Eqs. (27), (28), and (30) of that application, for the applied sources used in this example and Example 3, become:

$$q^f_A(t_{n+1}) = (1 - \Delta t \sigma_{sum}/2\varepsilon_0) q^f_A(t_n) - \Delta t \sigma_{diff}/4\pi\varepsilon_0 \Sigma_{i \neq A} q^f_i(t_n)$$
$$\Omega_{a \leftarrow i} \tag{5}$$

$$q^f_A(t_{n+1}) = (1 - \Delta t \sigma_{sum}/2\varepsilon_0) q^f_A(t_n) - \Delta t \sigma_{diff}/4\pi\varepsilon_0 \Sigma_{i \neq A} q^f_i(t_n)$$
$$\Omega_{a \leftarrow i} + I^f_A \Delta t \tag{6}$$

$$q^f_B = 0 \tag{7}$$

$$q^f_{int}(t_{n+1}) = (1 - \Delta t \sigma_{int}/\varepsilon_0) q^f_{int}(t_n) + I^f_{int} \Delta t, \tag{8}$$

where $\sigma_A$ is the conductivity on the higher conductivity side of the interface, $\sigma_B$ is the conductivity on the lower conductivity side, $\sigma_{int}$ is the conductivity at a location where an internal electrode (when used) introduces current ($I^f_{int}$) into the neural tissue, and $\sigma_{sum}$ and $\sigma_{diff}$ are given by:

$$\sigma_{sum} = \sigma_A + \sigma_B \tag{9}$$

$$\sigma_{diff} = \sigma_A - \sigma_B. \tag{10}$$

Eq. (5) was used for all the flattened calculation cells (pixels) except for those at a location where a surface electrode applied current to the surface of the scalp, where Eq. (6) was used. In those cases, $I^f_A$ was the total current introduced by the surface electrode divided by the number of flattened calculation cells used to represent the electrode. Four flattened calculation cells arranged as a square pad (15 mm×15 mm) were used for all of the surface electrodes (anode and cathode) except in the case of FIG. 19 where a strip anode composed of twenty flattened calculation cells arranged in a 2×10 array (15 mm×75 mm) was used. Thus, for the square pad, the electrode current, e.g., 1.0 milliamp, was divided by four to obtain $I^f_A$, while for the strip electrode, it was divided by twenty.

It should be noted that when Eq. (6) is used, the $q^f_A$ charges are a combination of electrode charges, i.e., charges on all or a part of an electrode, and charges in the flattened calculation cell due to charges in other calculation cells, i.e., other flattened calculation cells and internal calculation cells when used. On the other hand, when Eq. (8) is used, the $q^f_{int}$ charges are just electrode charges since internal calculation cells do not accumulate charges as a result of charges external to the calculation cell as discussed in paragraph [0062] of the '379 application (paragraph [0070] of the '282 publication). When the charges on the electrodes are in flattened calculation cells, those charges are the great majority of $q^f_A$. In the simulations of the figures of this example and Example 3, Eq. (6) was used for all electrodes except for the anode of FIG. 20 where Eq. (8) was used.

The charge distribution on sulcus 13 is typically unchanged whether current is applied using a surface electrode or an internal electrode at a nearby location. For example, a difference of less than 0.5% was found between the charge distributions on the sulcus between stimulation using pad electrodes at L0 and L40 on the surface of scalp layer 29 versus internal point source electrodes located 2.5 millimeters inboard of the left and right sides of the scalp layer's outer surface, but otherwise at the same locations.

Figure 15:
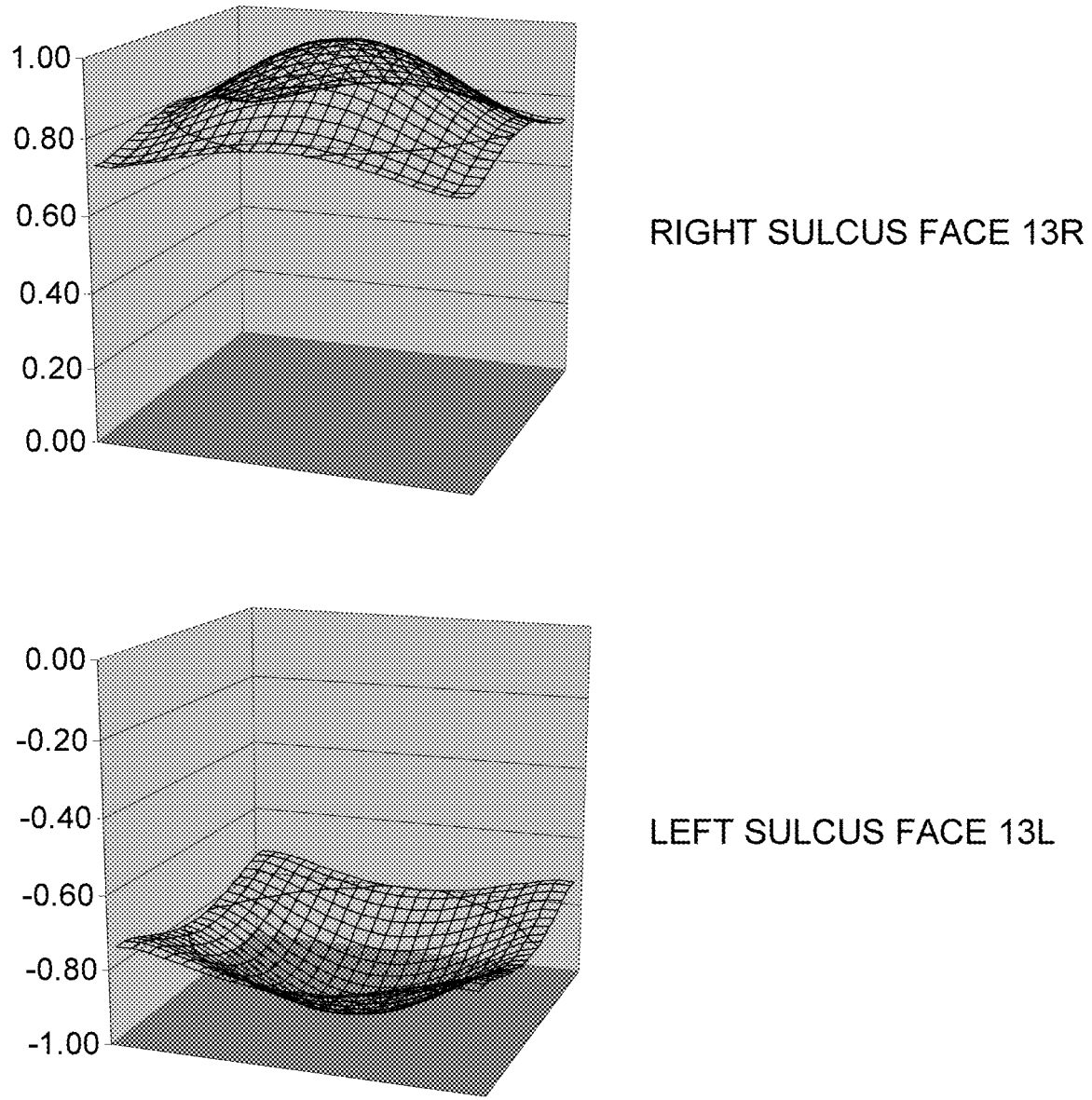
FIG. 15 shows normalized sulcus charge distributions for the right and left faces of sulcus 13 of FIG. 13 for a pad anode at location L0 and a pad cathode at location L40 in FIG. 13. In each of FIGS. 15-17 and 19-23, the upper topographical plot is for the right face of the sulcus and the lower plot for the left face. In each case, the top portion in FIG. 13 of sulcus 13 is at the front of the topographical plot. The rectangular geometry of FIG. 13 includes sharp corners that produce edge effects at the perimeters of the faces of the sulcus which have been cropped from the topographical plots. The normalization was the same for all of the plots, i.e., the charge/pixel values were divided by the charge/pixel value for Rt.Px.2 of FIG. 13 for the electrode locations of FIG. 15. The vertical scale of each plot of FIGS. 15-17 and 19-23 has been adjusted based on the range of normalized charge/pixel values produced by the electrode types and locations used in the figure.
Figure 16:
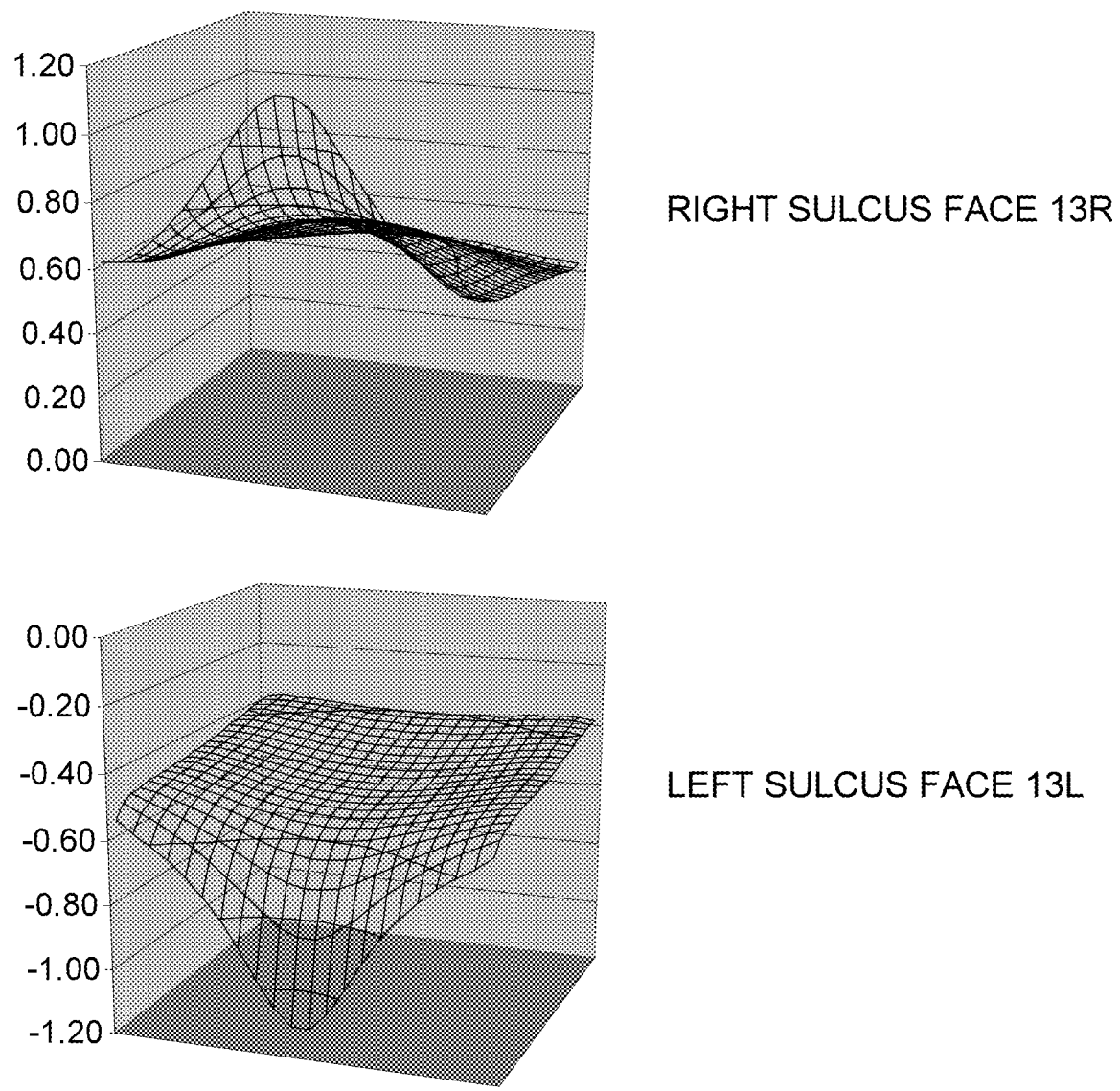
FIG. 16 shows normalized sulcus charge distributions for the right and left faces of the sulcus 13 of FIG. 13 for a pad anode at location L18 and a pad cathode at location L40 in FIG. 13.
Figure 17:
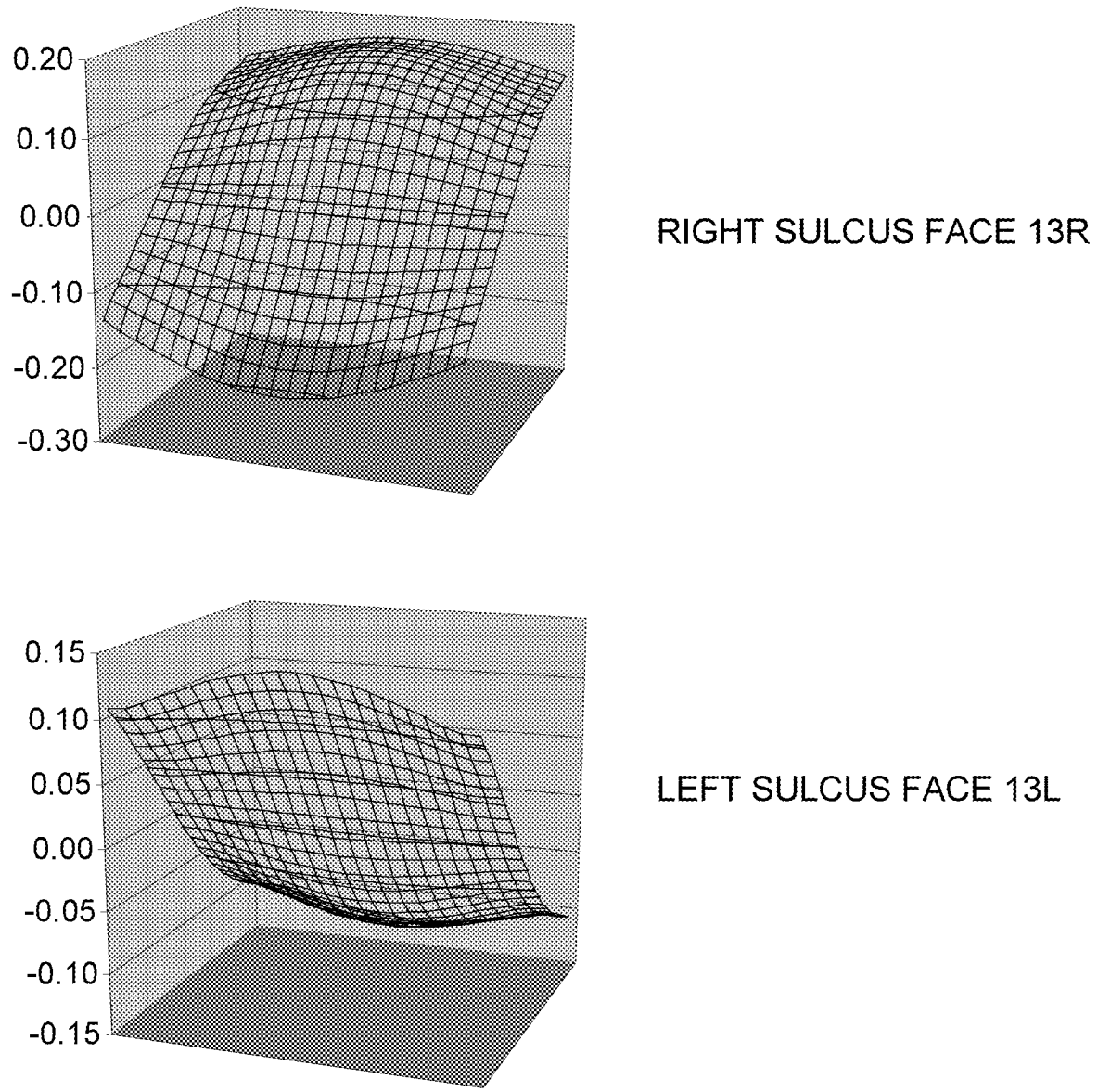
FIG. 17 shows normalized sulcus charge distributions for the right and left faces of the sulcus 13 of FIG. 13 for a pad anode at location L35 and a pad cathode at location L40 in FIG. 13.

FIGS. 15-18 illustrate the effect of electrode location on the charge distribution on the bounding surface of sulcus 13. The electrode locations are representative of some of those that are used in transcranial stimulation procedures. The upper panels of FIGS. 15-17 show the surface charge distribution for the sulcus's right face 13R, while the lower panels show the distribution for the left face 13L. The cathode was at the same location (L40) for each of these figures, while the anode was at L0 in FIG. 15, L18 in FIG. 16, and L35 in FIG. 17. Additional anode locations are set forth in FIG. 18 which plots charge/pixel values for the six flatten calculation cell locations (pixel locations) identified in FIG. 13 as Lt.Px.1, Rt.Px.1, Lt.Px.2, Rt.Px.2, Lt.Px.3, and Rt.Px.3 (hereinafter referred to as the "1-pixels", the "2-pixels", and the "3-pixels", respectively). In these figures, as well as in the rest of the plots of this example and those of Example 3, all charge values are normalized to the charge/pixel value for Rt.Px.2 for the anode at L0 and the cathode at L40, i.e., the symmetric case of FIG. 15 (referred to as the "normalization value" in the discussion of FIG. 24 below). For reference, in FIG. 15, the pixels of right sulcus face 13R prior to normalization had ~80,000 elementary charges for an applied current of 1.0 milliamp and Rt.Px.2 had ~200 of those elementary charges.

Figure 18A:
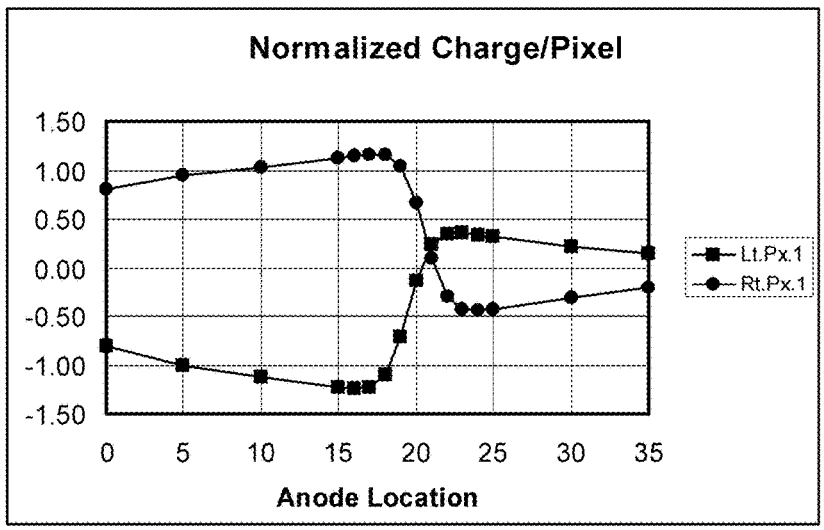
FIG. 18A shows normalized charge/pixel values at pixels Lt.Px.1 and Rt.Px.1 of sulcus 13 of FIG. 13 for a pad anode at locations L0 through L35 and a pad cathode at location L40 in FIG. 13.

The effects of electrode location shown in these figures, including the biphasic behavior of the 1-pixels in FIG. 18A, are readily understood in terms of the pixel-as-a-sensor process. Beginning with FIG. 15, the presence of positive charges on right sulcus face 13R follows immediately from the fact that the positive anode at L0 is in front of the higher conductivity side (CSF side) of this brain tissue/sulcus interface and the negative cathode at L40 is behind the higher conductivity side. Thus, the anode and the cathode work together to induce positive charges at right sulcus face 13R. For left sulcus face 13L, the locations of the electrodes relative to the higher conductivity side of the interface are just the opposite, the positive anode at L0 being behind the higher conductivity side (CSF side) and the negative cathode at L40 being in front of the higher conductivity side. The anode and cathode still work together, but now the effect is to induce negative charges at the left sulcus face 13L.

Figure 18B:
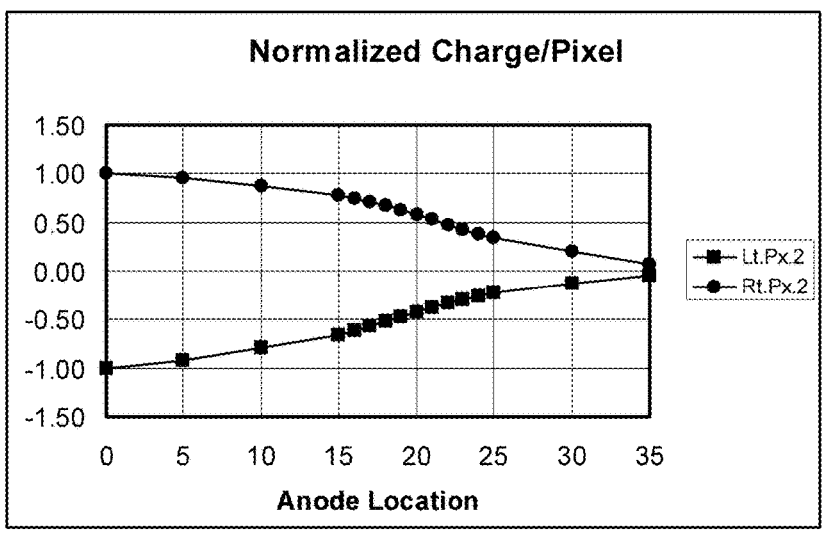
FIG. 18B shows normalized charge/pixel values at pixels Lt.Px.2 and Rt.Px.2 of sulcus 13 of FIG. 13 for a pad anode at locations L0 through L35 and a pad cathode at location L40 in FIG. 13.
Figure 18C:
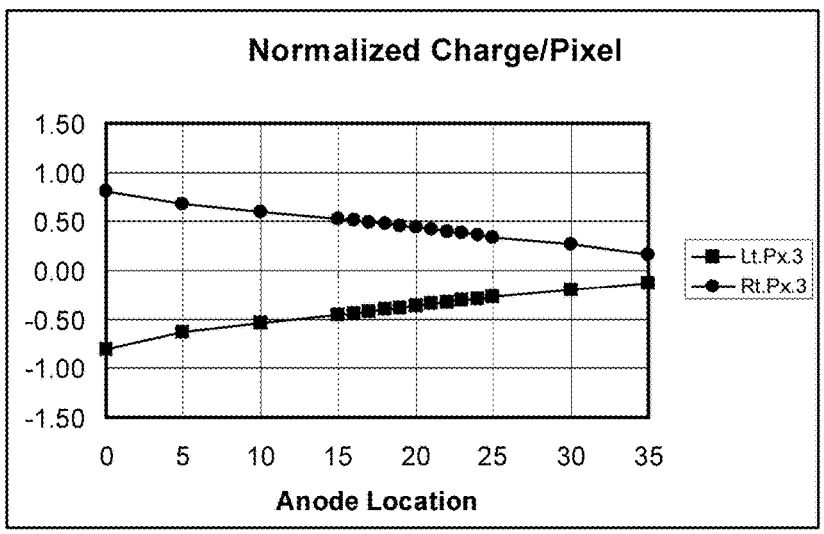
FIG. 18C shows normalized charge/pixel values at pixels Lt.Px.3 and Rt.Px.3 of sulcus 13 of FIG. 13 for a pad anode at locations L0 through L35 and a pad cathode at location L40 in FIG. 13.

The maximum solid angle magnitudes of interface pixels as seen from the charges on the electrodes at L0 and L40 are for the pixels at the centers of the sulcus faces, and thus the maximum charge/pixel magnitudes occur at those centers and drop off as one moves towards the edges of the faces (see FIG. 15). FIGS. 18A, 18B, and 18C further quantify this drop off. FIG. 15 corresponds to anode location 0 in FIG. 18. For this anode location, the magnitudes of the charge/pixel values for the 1-pixels and 3-pixels (FIGS. 18A and 18C) are smaller than the magnitudes of the values for the 2-pixels (FIG. 18B) because the 1-pixels and 3-pixels are near the edges of the sulcus faces and thus have smaller solid angle magnitudes than the 2-pixels as seen from the charges on the electrodes at L0 and L40. As can also be seen in FIG. 18, in view of the symmetry of the system, the charge/pixel values for the 1-pixels and 3-pixels are equal to one another for anode location 0.

As can be further seen in FIG. 18, as well as in FIGS. 16-17, as the anode moves along the surface of the scalp with the cathode held fixed at L40, the symmetry of the system is broken and the charge/pixel values at each of Lt.Px.1, Rt.Px.1, Lt.Px.2, Rt.Px.2, Lt.Px.3, and Rt.Px.3 becomes unique. Again, the responses at each of these pixels to changes in the location of the anode follows directly from the pixel-as-a-sensor process.

The most dramatic response occurs for the 1-pixels and thus we begin with them. As shown in FIG. 18A, as the anode moves along the scalp towards the location of the sulcus (anode location 20), the magnitudes of the charge/pixel values at both Lt.Px.1 and Rt.Px.1 increase. This follows from the fact that although the anode becomes less head-on to the 1-pixels as the anode moves towards the sulcus, which decreases the pixels' solid angle magnitudes as seen from the anode's charges, the distances to the pixels become smaller, which increases the solid angle magnitudes. Through anode location 18, where a maximum is reached, the distance effect dominates, and the solid angle magnitudes increase. These increasing solid angle magnitudes, in turn, result in increasing magnitudes for the charge/pixel values for these pixels.

However, once part of the anode lies over the sulcus, the obliquity of the pixels relative to the anode charges becomes dominant, it being recalled that when a pixel and a charge lie in the same plane, the charge cannot see the pixel. Thus, although the distance to the 1-pixels continues to decrease, the ability of the anode charges to see the 1-pixels (and the 2- and 3-pixels; see below) rapidly declines so that the solid angle magnitudes and consequently the magnitudes of the charge/pixel values, also rapidly decline as shown in FIG. 18A.

At anode location 20, the midline of the anode is directly over the midline of the sulcus, but because the anode is composed of four flattened calculation cells, two on each side of the anode's midline, with the charge of each the calculation cells being located at the center of the cell, and because the sulcus has a finite thickness, this anode location does not correspond to complete obliquity for the 1-pixels as seen by the charges of the electrode's calculation cells. Also, the charges on the cathode at L40, as well as those induced on the surfaces of scalp layer 29 and CSF layer 25 continue to induce charges at the 1-pixels, as do the charges of opposite sign on the opposing face of the sulcus. In terms of magnitudes, the charges on the cathode at L40 are the largest, and thus the net effect is for the charges on the left sulcus face to be negative and those on the right sulcus face to be positive for anode location 20, as they were for anode locations 0 through 19. Because Rt.Px.1 is closer to the cathode at L40 than Lt.Px.1, the magnitude of the charge/pixel value for Rt.Px.1 is larger than that for Lt.Px.1, as can be seen in FIG. 18A.

Once the anode moves to the right of the sulcus, rather than working together, the charges on the anode and the cathode are in competition in terms of their effects on the 1-pixels. While the cathode continues to seek to induce positive charges at Rt.Px.1 and negative charges at Lt.Px.1, the anode now seeks to induce negative charges at Rt.Px.1 and positive charges at Lt.Px.1. Because the anode is closer to the 1-pixels than the cathode, its effects dominate and thus Lt.Px.1 turns positive and Rt.Px.1 turns negative as the anode moves to locations completely over right hemisphere 23.

At anode location 21, where part of the anode is still over the sulcus, the 1-pixels and, in particular, Rt.Px.1 is highly oblique to the charges on the anode and thus the effects of those charges are diminished. Consequently, for this anode location, Rt.Px.1 and Lt.Px.1 are both positive. As the anode moves further to the right of the sulcus, the obliquity with respect to the charges on the anode of the 1-pixels and, in particular, that of Rt.Px.1 becomes less and more like the obliquity with respect to the charges on the cathode. The proximity effect then dominates and since the 1-pixels are closer to the anode than the cathode, the charges of Rt.Px.1 are negative since the anode is behind the higher conductivity side of the sulcus/right hemisphere interface and the charges of Lt.Px.1 are positive since the anode is in front of the higher conductivity side of the sulcus/left hemisphere interface.

As shown in FIGS. 18B and 18C, the behavior of the 2- and 3-pixels are simpler than the behavior of the 1-pixels. In overview, the cathode at L40 dominates the behavior of these pixels since this electrode is head-on to the 2-pixels and has a less oblique relationship with the 3-pixels than the anode for all locations of the anode, except for the L0 location where the obliquities are the same. Thus, Rt.Px.2 and Rt.Px.3 are positive and Lt.Px.2 and Lt.Px.3 are negative since the "stronger-in-terms-of-solid-angle" negative cathode is behind (in front of) the higher conductivity side of the sulcus's right (left) face. The charges on the anode cooperate with those on the cathode for anode locations 0-20 and then compete for anode locations 21-35.

The behavior at anode location L35 for the 1-, 2-, and 3-pixels further illustrates the usefulness of the pixel-as-a-sensor process in interpreting and predicting charge distributions. Thus, referring to FIG. 13 and using the pixel-as-a-sensor process, one can see that Lt.Px.1 should be positive and Rt.Px.1 should be negative because for the anode at location L35, these pixels are closer to the anode than to the cathode and the anode is on the higher (lower) conductivity side of the left (right) pixel. For the 2- and 3-pixels, on the other hand, the negative cathode at L40 is the closest electrode and thus we should see the opposite charges, i.e., the right pixels should be positive and the left pixels negative. This is exactly what FIG. 18 shows, i.e., in FIG. 18A, for anode location L35, Lt.Px.1 is positive and Rt.Px.1 is negative, while in FIG. 18B, Lt.Px.2 is negative and Rt.Px.2 is positive, and likewise in FIG. 18C, Lt.Px.3 is negative and Rt.Px.3 is positive. Thus in selecting locations for electrodes when applying electrical current to neural tissue, the pixel-as-a-sensor process provides an effective way to determine the type of charge distributions that will result from any particular choice of electrode locations.

FIGS. 16 and 17 provide further insight into the plots of FIG. 18. Thus, FIG. 16 illustrates that the charge distribution is positive at all locations on the right face 13R of the sulcus and negative at all locations on the left face 13L for anode location L18 as can also be seen in FIGS. 18A, 18B, and 18C for that anode location. FIG. 17, on the other hand, shows that for anode location L35, the charge changes sign from negative to positive as one moves down the right face 13R of the sulcus (corresponding to moving from front to back in the figure) and from positive to negative as one moves down the left face 13L (again corresponding to moving from front to back in the figure). This same behavior is shown in FIGS. 18A, 18B, and 18C for anode location L35. FIG. 17 also shows that when the anode and cathode are on the same side of a sulcus, the charge magnitudes are significantly reduced by the competition effect compared to the magnitudes when the anode and cathode are on opposite sides of a sulcus and cooperate in inducing charges on the sulcus's bounding surface (compare the scales of FIG. 17 with those of FIGS. 15 and 16).

Figure 19:
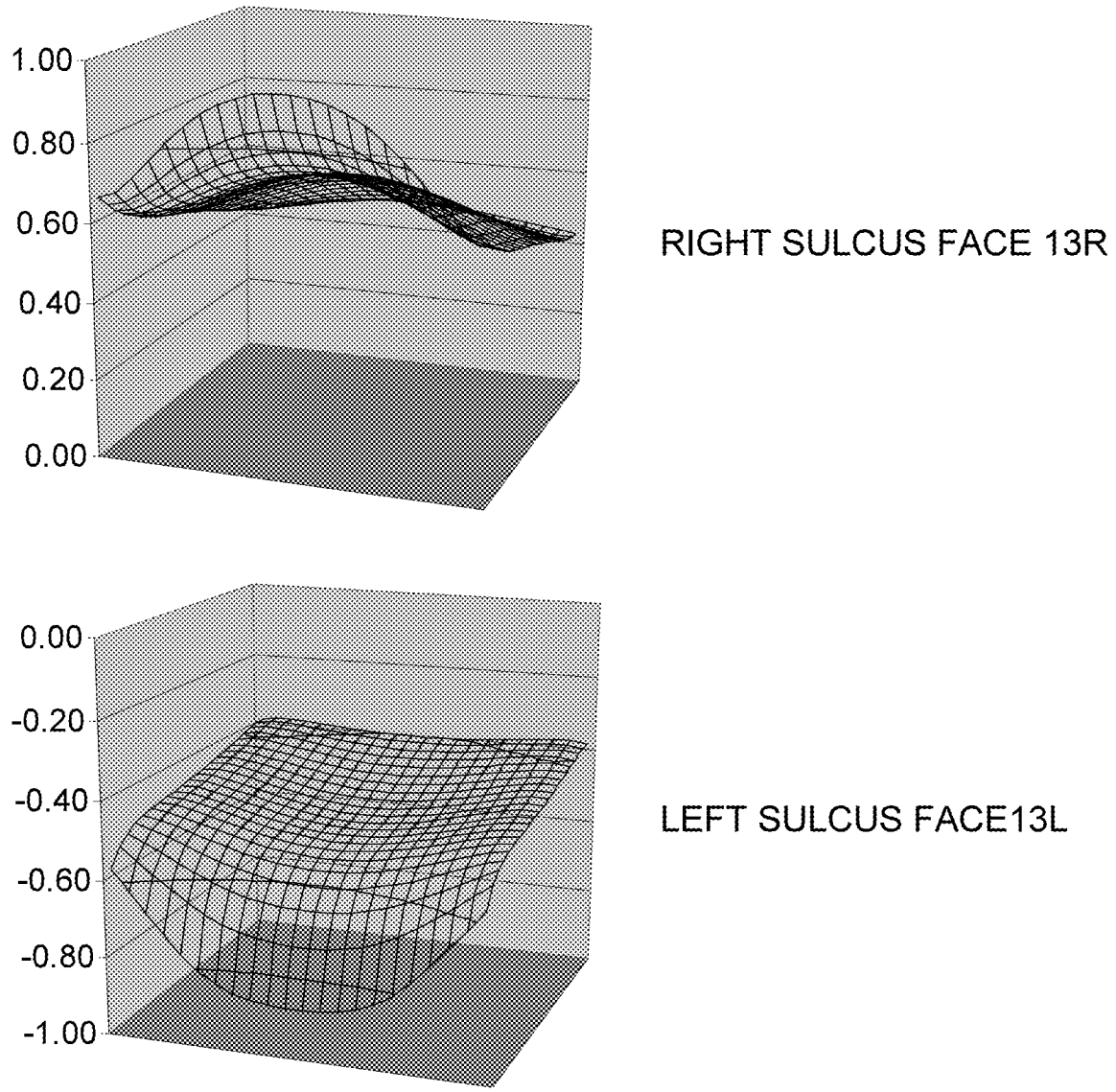
FIG. 19 shows normalized sulcus charge distributions for the right and left faces of the sulcus 13 of FIG. 13 for a strip anode at location L18 and a pad cathode at location L40 in FIG. 13.
Figure 20:
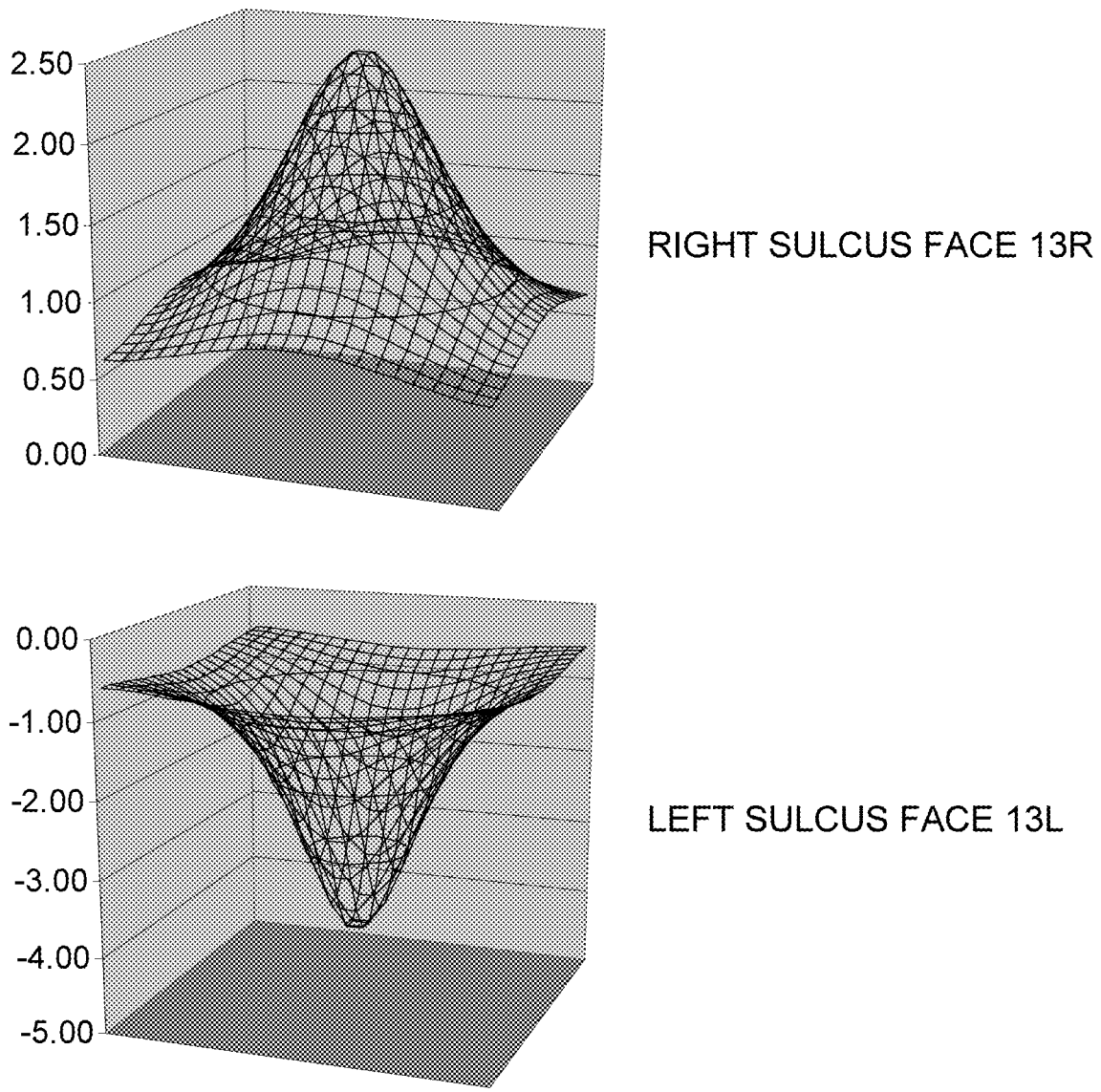
FIG. 20 shows normalized sulcus charge distributions for the right and left faces of the sulcus 13 of FIG. 13 for a point source anode at PtSr and a pad cathode at location L40 in FIG. 13.

FIGS. 19 and 20 illustrate the effects of electrode configuration on the induced charges. Specifically, FIG. 19 uses a strip anode (2×10 pixels) at L18 extending perpendicular to and bisected by the plane of FIG. 13 in place of the pad anode (2×2 pixels) of FIG. 16. For the use of a strip electrode oriented parallel to a sulcus see Parazzini et al., "A Computational Model of the Electric Field Distribution due to Regional Personalized or Non-Personalized Electrodes to Select Transcranial Electric Stimulation Target," *IEEE Transactions on Biomedical Engineering*, Vol. 64, January 2017, pages 184-195. Qualitatively, the charge distributions of FIG. 19 (strip anode) and FIG. 16 (pad anode) are quite similar being all positive for the right sulcus face 13R and all negative for the left sulcus face 13L with the largest magnitudes being at the portion of the faces closest to the anode. Those largest magnitudes, however, are both smaller and less concentrated with the strip anode (FIG. 19) than the pad anode (FIG. 16).

These differences follow directly from the pixel-as-a-sensor process. Thus, although the strip electrode carries the same amount of current as the pad electrode, that current is spread out over twenty calculation cells rather than being concentrated in four cells. This means that the charges per calculation cell are smaller for the strip electrode than the pad electrode which, in turn, means a less concentrated inducement of charge at any particular location on the bounding surface of the sulcus. However, because the electrode charges have a wider spatial distribution, they can have a head-on solid angle effect on a larger portion of the bounding surface of the sulcus. Thus, in FIG. 19, we see lower, but more widely-distributed, charge magnitudes near the strip anode than seen near the pad anode in FIG. 16.

FIG. 20 illustrates the case of an anode located within a subject's brain tissue, as in the case of deep brain stimulation. See, for example, Butson et al., "Patient-Specific Analysis of the Volume of Tissue Activated During Deep Brain Stimulation," *Neuroimage*, 2007, Vol. 34, pages 661-670. Specifically, for this figure, the anode was a point source at the center of left hemisphere 21 (see PtSr in FIG. 13). This point source introduced the same amount of current into the system as a surface electrode but, as can be clearly seen in FIG. 20, produced a much stronger response on the bounding surface of the sulcus than a surface electrode (compare the scale of FIG. 20 with, for example, that of FIG. 15).

This difference can be understood as follows. Beginning with the configurations of the anodes in the two cases, for a point source in an internal calculation cell, the current can flow out of all of the calculation cell's faces, i.e., the magnitude of the solid angle for outward flux is 4n. On the other hand, for a surface electrode at the scalp/air interface represented by one or more flattened calculation cells, current can only flow out of the scalp side faces of the calculation cells, i.e., the magnitude of the solid angle for outward flux is 2n. Thus, if the conductivities were the same at the point source and surface electrodes, the charge needed to produce the current at the point source would be ½ that needed at the surface electrode.

However, the conductivity of the brain tissue at the point source of FIG. 20 was substantially less than the conductivity of the scalp at the surface electrode of FIG. 15. As shown in, for example, Eq. (4) above, the charge on an electrode varies inversely with the conductivity of the tissue in which the electrode resides. For the parameters used in this simulation, the scalp had a conductivity slightly greater than twice that of the brain tissue (i.e., 0.465 S/m versus 0.200 S/m; see above), so that the charge on the electrode in the brain tissue should be approximately twice that on the scalp, specifically, ~2.3 times greater. However, as noted above, flattened calculation cells of a surface electrode accumulate charge not only because they are receiving applied current but also as a result of charges in other calculation cells in the system, while internal calculation cells do not accumulate such extra charge. The net effect for this simulation was that at steady state the anode in FIG. 20 had $2.8 \times 10^5$ elementary charges for one milliamp of current while the four flattened calculation cells of the anode of FIG. 15 had about 7% more charges for the same current, i.e., a total $3.0 \times 10^5$ elementary charges.

Although it had slightly less charges, the point source anode was much closer to the bounding surface of the sulcus than the surface anode of FIG. 15. Accordingly, the solid angles of the sulcus's surface pixels as seen from the charges of the point source and, in particular, the pixels at the center of the sulcus's right and left faces, were larger (on the order of 6 times larger) than the solid angles seen from the charges of the surface electrode. As discussed above, larger solid angles mean larger induced charges. In addition to this proximity effect, the surface anode of FIG. 15 induces positive charges at the scalp/skull interface, negative charges at the skull/CSF interface, and positive charges at the CSF/brain tissue interface, while the point source anode being on the right side of these interfaces rather than the left (see FIG. 13), produces charges of the opposite sign. The pixels of the sulcus's bounding surface sense all of these charges and adjust their charges to achieve steady state. As shown in FIG. 20, the net effect is charge/pixel values at Rt.Px.2 and Lt.Px.2 whose magnitudes are ~2.4 and ~4.0 times greater than those for FIG. 15.

In summary, as illustrated in this Example 2, varying the locations of the electrodes used to apply electrical current to neural tissue, as well as varying electrode configurations, results in substantial changes in the charge distributions induce on the bounding surfaces of sulci thus allowing customization of neural tissue stimulation for particular physiological goals and/or personalization of the stimulation for particular subjects. See, for example, "Automated MRI segmentation for individualized modeling of current flow in the human head," *J. Neural. Eng.* 2013, Vol. 10, pages 1-26; Kim et al., "Inconsistent outcomes of transcranial direct current stimulation (tDCS) may be originated from the anatomical differences among individuals: A simulation study using individual MRI data," *Engineering in Medicine and Biology Society* (EMBC), 2013 35th Annual International Conference of the IEEE, July 2013, pages 823-825; Russell et al., "Individual differences in transcranial electrical stimulation current density," *The Journal of Biomedical Research*, 2013, Vol. 27, pages 495-508; and Russell et al., "Gender differences in current received during transcranial electrical stimulation," *Frontiers in Psychiatry*, August 2014, Vol. 5, pages 1-7.

Example 3

This example illustrates the effects on a sulcus charge distribution of a region that neighbors the sulcus and has a conductivity different from that of the region's surrounding neural tissue. The region can, for example, be a ventricle, a neighboring sulcus, or a CSF-filled void resulting from a stroke. See, for example, Datta et al., "Individualized model predicts brain current flow during transcranial direct-current stimulation treatment in responsive stroke patient," *Brain Stimulation*, Vol. 4, pages 169-174, 2011. In each of these representative, but not limiting, examples, the neighboring region will have the conductivity of CSF. Regions having lower or higher conductivities than CSF will have similar effects, the size and sign of the effect depending on the difference between the region's conductivity and the conductivity of the region's surrounding neural tissue. Such non-CSF regions can be naturally occurring (e.g., neural regions having locally higher or lower conductivities) or can result from the presence of non-naturally occurring materials (e.g., implants) in the subject's neural tissue, e.g., in the subject's brain or spinal cord.

Figure 21:
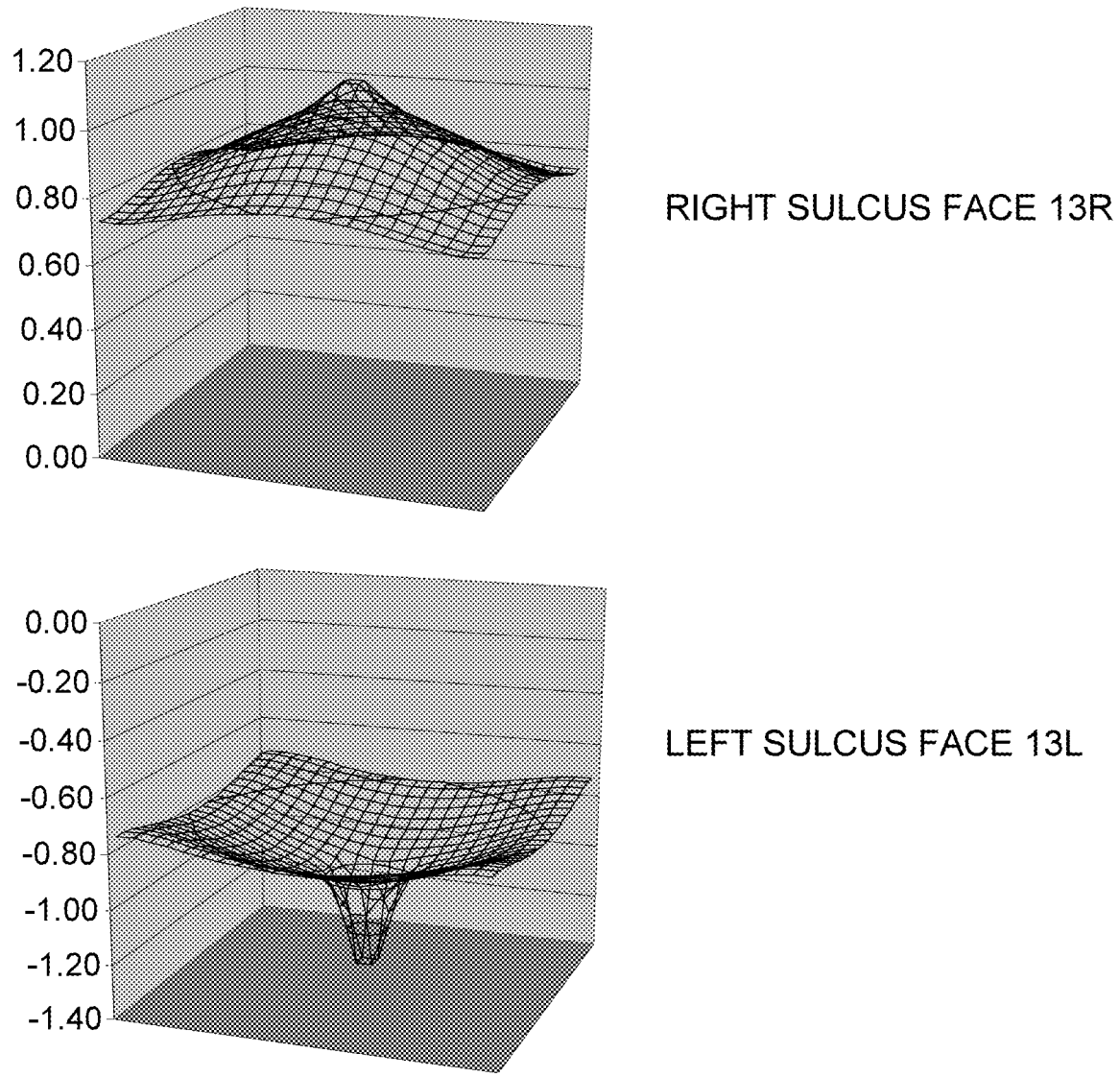
FIG. 21 shows normalized sulcus charge distributions for the right and left faces of sulcus 13 of FIG. 13 for a pad anode at location L0, a pad cathode at location L40, and a 1×1×1 cm$^3$ CSF region at D=5 mm in FIG. 13.
Figure 22:
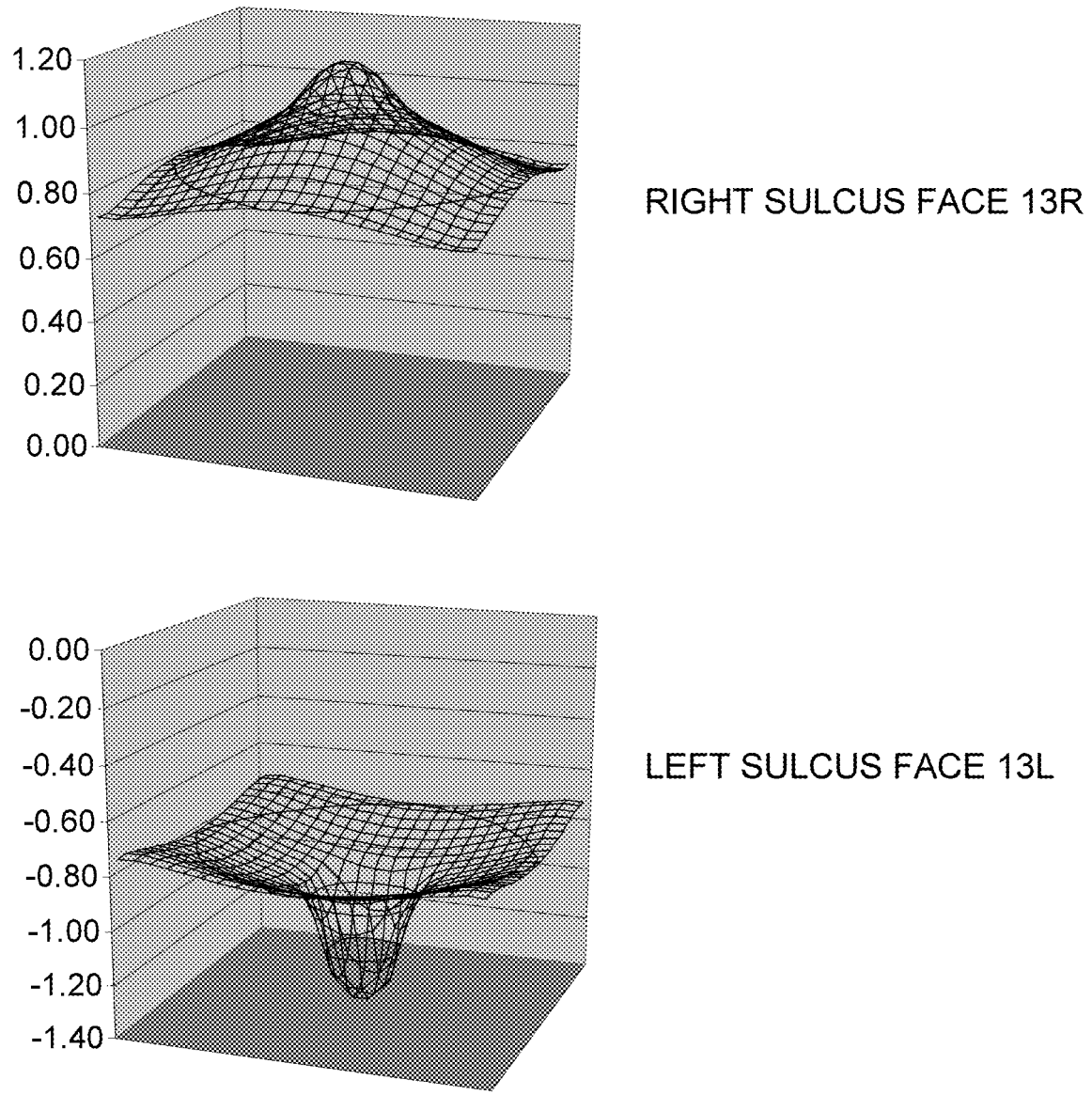
FIG. 22 shows normalized sulcus charge distributions for the right and left faces of sulcus 13 of FIG. 13 for a pad anode at location L0, a pad cathode at location L40, and a 2×2×1 cm$^3$ CSF region at D=5 mm in FIG. 13.
Figure 23:
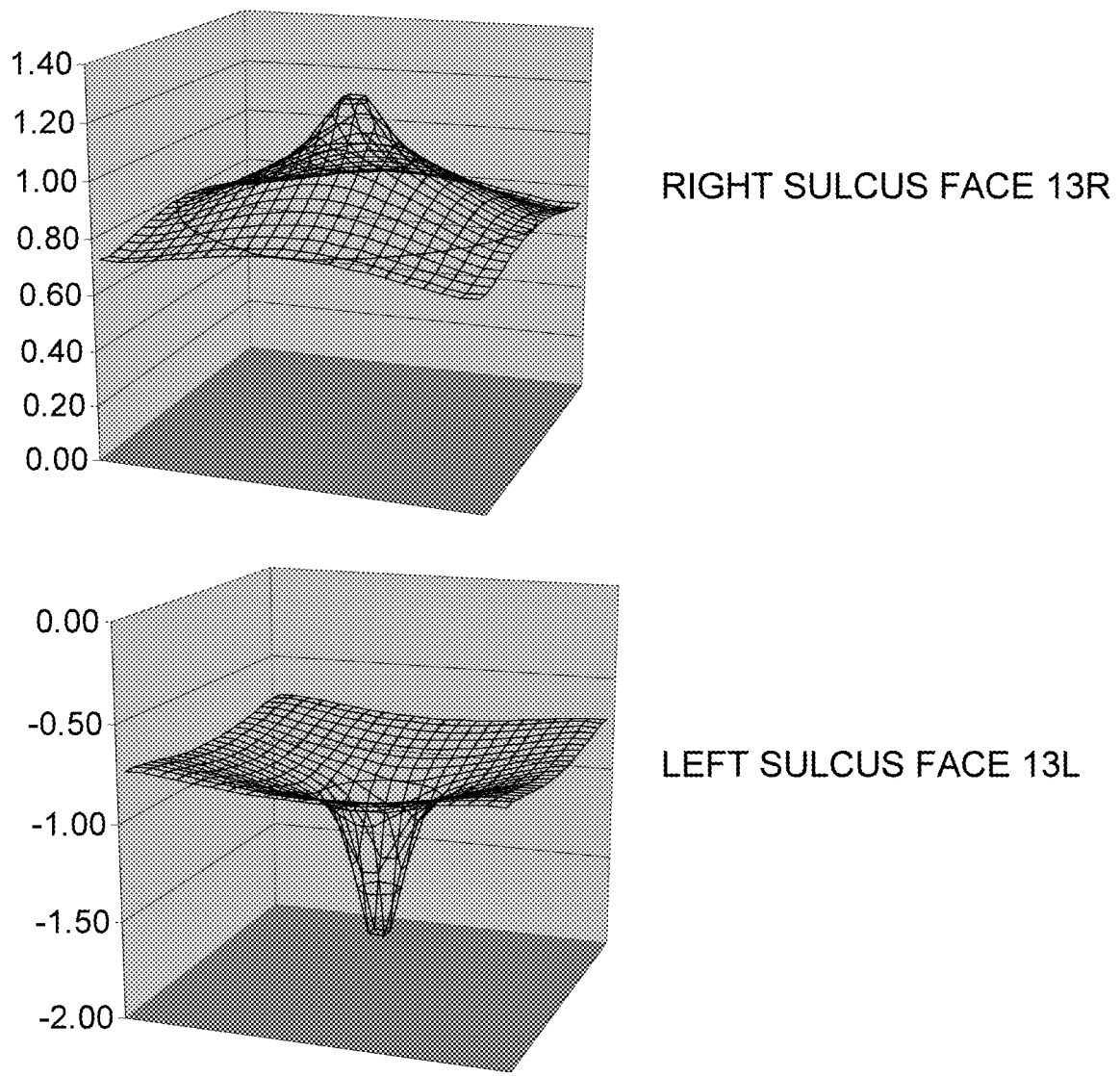
FIG. 23 shows normalized sulcus charge distributions for the right and left faces of sulcus 13 of FIG. 13 for a pad anode at location L0, a pad cathode at location L40, and a 1×1×4 cm$^3$ CSF region at D=5 mm in FIG. 13.

FIGS. 21-23 show the effects of a CSF region 31 located in left hemisphere 21 of FIG. 13 at a distance D from the left face 13L of sulcus 13. For FIGS. 21-23, D was 5 mm. For FIG. 21, the region was a 1×1×1 cm$^3$ cube, while for FIG. 22, it was 2×2×1 cm$^3$ parallelepiped with the first two dimensions being parallel to and the third dimension perpendicular to the face of the sulcus, i.e., in FIG. 22, the region was wider than it was deep. For FIG. 23, the region was a 1×1×4 cm$^3$ parallelepiped, i.e., it was deeper than it was wide. The square pixels used to represent the surfaces of these regions had an edge length of 2.5 millimeters, so that 96 pixels were used for the surface of the FIG. 21 region, 256 for the surface of the FIG. 22 region, and 288 for surface of the FIG. 23 region.

As can be seen in FIGS. 21-23, the presence of region 31 locally increased the magnitude of the charge distributions on the left and right faces 13L,13R of the sulcus, with the right face becoming locally more positive and the left face locally more negative, with the local change in magnitude of the left face being greater than that of the right face. As can be further seen, the 2×2×1 cm$^3$ region of FIG. 22 affected larger areas of the sulcus faces than the 1×1×1 cm$^3$ and the 1×1×4 cm$^3$ regions of FIGS. 21 and 23. On the other hand, the 1×1×4 cm$^3$ region of FIG. 23 had a stronger effect on the charge distribution than either the 1×1×1 cm$^3$ or the 2×2×1 cm$^3$ regions of FIGS. 21 and 23.

These responses at the sulcus faces to the presence of a neighboring region having the conductivity of cerebrospinal fluid follow directly from the pixel-as-a-sensor process. Referring to FIG. 13, as seen from an anode at L0 and a cathode at L40, the left hand and right hand panels of region 31 will have the largest solid angles and thus will develop the largest induced charges, the charges on the left hand panel of region 31 being negative because the anode (cathode) is behind (in front of) the higher conductivity side of the panel and the charges on the right hand panel of region 31 being positive because the anode (cathode) is in front of (behind) the higher conductivity side of the panel.

These charges on the panels of region 31 act as further sources that induce charges on the faces of the sulcus. Because the right hand panel of region 31, which has a positive charge, is closer to the faces of the sulcus than the left hand panel of region 31, the region will act like another anode to the sulcus. Hence, locally (i.e., primarily where the region is located), the region will induce negative charge on the left sulcus face 13L and positive charge on the right sulcus face 13R, as seen in each of FIGS. 21-23.

Because the right hand panel of region 31 is closer to left sulcus face 13L than right sulcus face 13R, the effect on the charge distribution is stronger for the left sulcus face than the right sulcus face, as also seen in each of FIGS. 21-23. Moving region 31 from its on-axis position of FIG. 13 to an off-axis position moves the location of the effects on the sulcus faces due to the presence of the region without changing the qualitative nature of those effects (data not shown). Likewise, multiple regions induce multiple effects on the sulcus's charge distribution, the effects being additive but, in general, not linearly additive because of interactions between charges of one region with charges of other regions and with charges on the faces of the sulcus. For example, a second region in right hemisphere 23 located symmetrically to region 31 acts as another cathode to the sulcus and thus locally increases the magnitudes of the charges on the faces of the sulcus in the same manner as region 31. Although the combined effect of the two regions is greater than the effect of either region alone, the combined effect is less than twice the effect of a single region because of mutual interactions between induced charges of the regions and the sulcus.

With specific regard to FIG. 22, when region 31 has the 2×2×1 cm$^3$ parallelepiped configuration of that figure, the anode at L0 and the cathode at L40 induce charges over the larger areas of the region's left and right hand panels (i.e., an area of 4 cm$^2$ in FIG. 22 versus an area of 1 cm$^2$ in FIG. 21). These induced charges over larger areas, in turn, induce charges over larger areas of the left and right sulcus faces as can be seen by comparing the plots of FIG. 22 with those of FIG. 21.

FIG. 23 returns to the 1 cm$^2$ areas for the left and right hand panels of region 31, but now those panels are separated by 4 cm, rather than just 1 cm. The larger magnitudes of induced charge for this configuration arise from the fact that while the right hand panel of region 31 is still 5 mm from left sulcus face 13L, the left hand panel of the region is now 45 mm from the left sulcus face (and thus 47 mm from the right sulcus face). The left hand panel of region 31 develops a charge opposite to that of the right hand panel, i.e., a negative charge, since anode L0 (cathode L40) is behind (in front of) the higher conductivity side of the panel. This negative charge on the left hand panel of region 31 tends to reduce the effects of the positive charge on the right hand panel of the region. By moving this negative charge of the left hand panel further from the sulcus, its effect is reduced thus allowing the positive charge of the right hand panel to have an increased effect on the sulcus. In the end, as shown FIG. 23, the 1×1×4 cm$^3$ configuration for region 31 produces substantially larger magnitudes of induced charges on the faces of the sulcus than either the 1×1×1 cm$^3$ or 2×2×1 cm$^3$ configurations.

Figure 24:
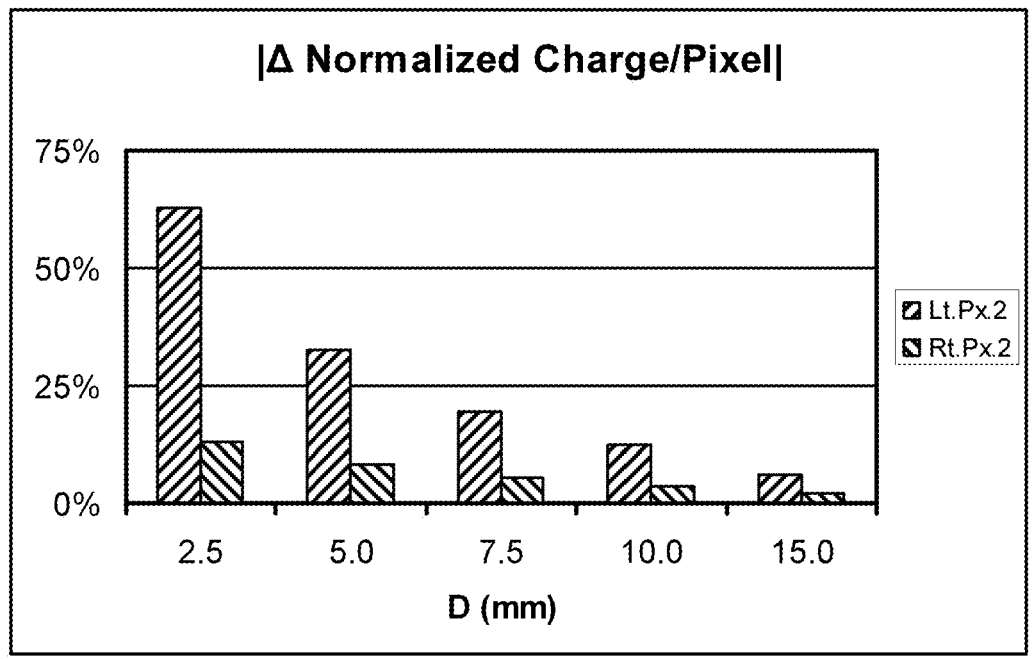
FIG. 24 is plot showing the magnitude of the percentage change in normalized charge/pixel values at pixels Lt.Px.2 and Rt.Px.2 of FIG. 13 for a pad anode at location L0 and a pad cathode at location L40 between: (i) the case of no CSF region and (ii) the cases of a 1×1×1 cm$^3$ CSF region at D=2.5, 5.0, 7.5, 10.0 and 15.0 mm in FIG. 13.

FIG. 24 examines the effects of changes in the distance D between region 31 and left sulcus face 13L. The effects are reported as percentage changes in the charge/pixel values for Lt.Px.2 and Rt.Px.2 from the normalization value, i.e., the value of Rt.Px.2 for the FIG. 15 case (see above). As in FIG. 21, region 31 was a 1×1×1 cm$^3$ cube. As shown in FIG. 24, region 31's effect is stronger at Lt.Px.2 than at Rt.Px.2 for all values of D, and for each pixel, the effect declines as the region moves farther from the sulcus, i.e., as D increases.

Figure 25:
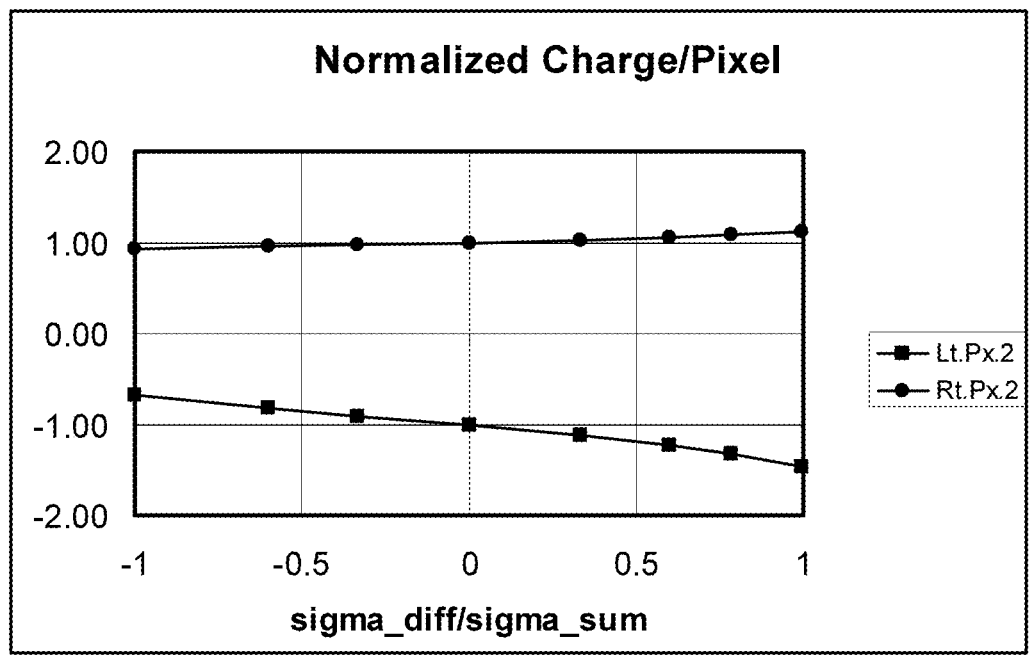
FIG. 25 is a plot of normalized charge/pixel values for a pad anode at location L0, a pad cathode at location L40, and a 1×1×1 cm$^3$ region at D=5 mm in FIG. 13 as a function of the region's conductivity expressed as sigma_diff/sigma_sum, where sigma_sum and sigma_diff are, respectively, $\sigma_{sum}$ and $\sigma_{diff}$ of Eqs. (9) and (10).

FIG. 25 examines the effects of changes in the conductivity of region 31. As one example, tumors are known to be associated with an increase in the conductivity of the affected tissue. See Song et al., "Numeric Investigation of Brain Tumor Influence on the Current Distributions During Transcranial Direct Current Stimulation," *IEEE Transactions on Biomedical Engineering*, Vol. 63, No. 1, January 2016, pages 176-187.

As in FIG. 21, region 31 was a 1×1×1 cm$^3$ cube located 5 mm to the left of left sulcus face 13L in FIG. 13 (D=5 mm). The effects of the value of region 31's conductivity are reported in FIG. 25 terms of the normalized charge/pixel values at Lt.Px.2 and Rt.Px.2 versus the ratio R:

$$R = \sigma_{diff}/\sigma_{sum} = (\sigma_{region} - \sigma_{neural})/(\sigma_{region} + \sigma_{neural}), \quad (11)$$

where $\sigma_{region}$ is the conductivity of the region and $\sigma_{neural}$ is the conductivity of the surrounding medium.

For a region having the same conductivity as the surrounding medium, this ratio is zero, while for regions having a conductivity greater than (less than) the surrounding medium, the ratio is positive (negative). The maximum and minimum values for the ratio are +1 and −1, corresponding to, for example, a region 31 composed of metal (essentially +1) or plastic (essentially −1).

For a CSF conductivity of 1.650 S/m and a neural conductivity (brain conductivity) of 0.200 S/m, i.e., the values used for the other plots of this example, the ratio is 0.784, i.e., the next to the last Lt.Px.2 and Rt.Px.2 data points at the right side of FIG. 25. These data points correspond to the FIG. 21 configuration and, as in that figure, the effect of the region 31 is substantially smaller for Rt.Px.2 than for Lt.Px.2 (see also the D=5 mm data points of FIG. 24.)

This reduced effect at Rt.Px.2 compared to Lt.Px.2 is seen throughout the ±1 range of R, the magnitude of the charge/pixel value for Rt.Px.2 being only 7.4 percent less for R=−1 ($\sigma_{region}$=0 S/m) than for R=0 ($\sigma_{region}$=0.200 S/m) and only 11.9 percent greater for R=+0.996 ($\sigma_{region}$=100.0 S/m), while for Lt.Px.2, the percentage changes are 31.7 percent less for R=−1 ($\sigma_{region}$=0 S/m) and 46.9 percent greater for R=+0.996 ($\sigma_{region}$=100.0 S/m).

In terms of clinical practice, these results demonstrate that conductive/non-conductive implant(s), e.g., metal/plastic implant(s), can be used to steer charge accumulations towards or away from the bounding surface(s) of one or more sulci or part(s) thereof or towards or away from other neural structures of interest. The results also show that the effects of an implant are (i) mostly localized to the structures closest to the implant (see, for example, the first data points of FIG. 24 where the effects on Rt.Px.2 are ~5 times smaller than the effects on Lt.Px.2) and (ii) bounded in terms of the ability of the implant's conductivity to affect the sulcus's charge distribution since R cannot drop below −1 or rise above +1. As shown in FIG. 25, the charge distribution is well-behaved at these limiting values, i.e., the charge/pixel values do not exhibit an exponential or other rapid rise or fall as R approaches these limits. The use of one or more temporary and/or permanent implants having the same conductivity as one another or different conductivities provides an effective way to tailor the effects of electrical stimulation of neural tissue to the needs of individual subjects.

Recent summaries of the types of diseases that will benefit from the processes disclosed herein include: Miranda et al., "Optimizing Electric-Field Delivery for tDCS: Virtual Humans Help to Design Efficient, Noninvasive Brain and Spinal Cord Electrical Stimulation," *IEEE Pulse*, Vol. 8, July/August 2017, pages 42-45, which discusses how transcranial DC stimulation has been the subject of clinical trials relating to pain, depression, post-stroke rehabilitation, dystonia, multiple sclerosis, epilepsy, dementia, schizophrenia, autism, and attention disorders; Lefaucheur, J-P., "A comprehensive database of published tDCS clinical trials (2005-2016)," *Clinical Neurophysiology*, 2016, Vol. 46, pages 319-398, which lists over three hundred references relating to the application of transcranial DC stimulation to the foregoing problems and such other clinical challenges as Parkinson's disease, cerebral palsy, primary progressive aphasia, consciousness disorders, Alzheimer's disease, tinnitus, addiction, and craving; and Kirsch, et al., "Cranial Electrotherapy Stimulation for Treatment of Anxiety, Depression, and Insomnia," *Psychiatr. Clin. N. Am.*, 36 (2013), pages 169-176, which highlights the clinical use of cranial electrotherapy in connection with psychiatric disorders. In addition to its use in connection with diseases, transcranial electrical stimulation has also been used to enhance the performance of healthy subjects, e.g., athletes (see Strickland, E., "A New Kind of Juice," *IEEE Spectrum*, Vol. 53, September 2016, pages 34-40), and the processes of the present disclosure will also be of benefit in these applications.

Although in the preferred embodiments, electrical current is applied to the neural tissue, in many cases, calculating and displaying a charge distribution for at least a part of the bounding surface of a sulcus without applying current will be of value in selecting a course of treatment for a subject suffering from one or more of the numerous physical and mental illnesses that have been found responsive to electrical stimulation. For example, the display of a calculated charge distribution will be useful in deciding if a particular subject will benefit from or be harmed by electrical stimulation, e.g., a display of the charge distribution may reveal the likelihood that the application of current may result in adverse side effects, e.g., an epileptic episode in a subject susceptible to such episodes as a result of a charge accumulation at a location in the subject's brain known or suspected to be an origin of the episodes.

When used in this way, i.e., without the application of current, the disclosure provides, in one embodiment, a computer-implemented method for modeling/simulating the effects of applying electrical current to a neural tissue using at least two electrodes, the neural tissue having at least one sulcus filled with cerebrospinal fluid, the method comprising calculating and displaying, using a computer, a charge distribution for at least a part of the bounding surface of the sulcus, said charge distribution originating at least in part from charges on at least part of an electrode. In another embodiment, the disclosure provides a computer-implemented method for modeling/simulating the effects of applying electrical current to a neural tissue using at least two electrodes, the neural tissue having at least one sulcus filled with cerebrospinal fluid, the method comprising calculating and displaying, using a computer, a charge distribution for at least a part of the bounding surface of the sulcus, said charge distribution depending at least in part on a location for at least one of the electrodes relative to the sulcus. In each case, the display of the calculated charge distribution or a portion thereof can serve as an aid in deciding an appropriate course of treatment, electrical or otherwise, for a subject. In certain embodiments, modeling/simulating the effects of applying electrical current to a neural tissue can employ the pixel-as-a-sensor process either alone or in combination with displaying a charge distribution or a portion thereof.

Figure 26:
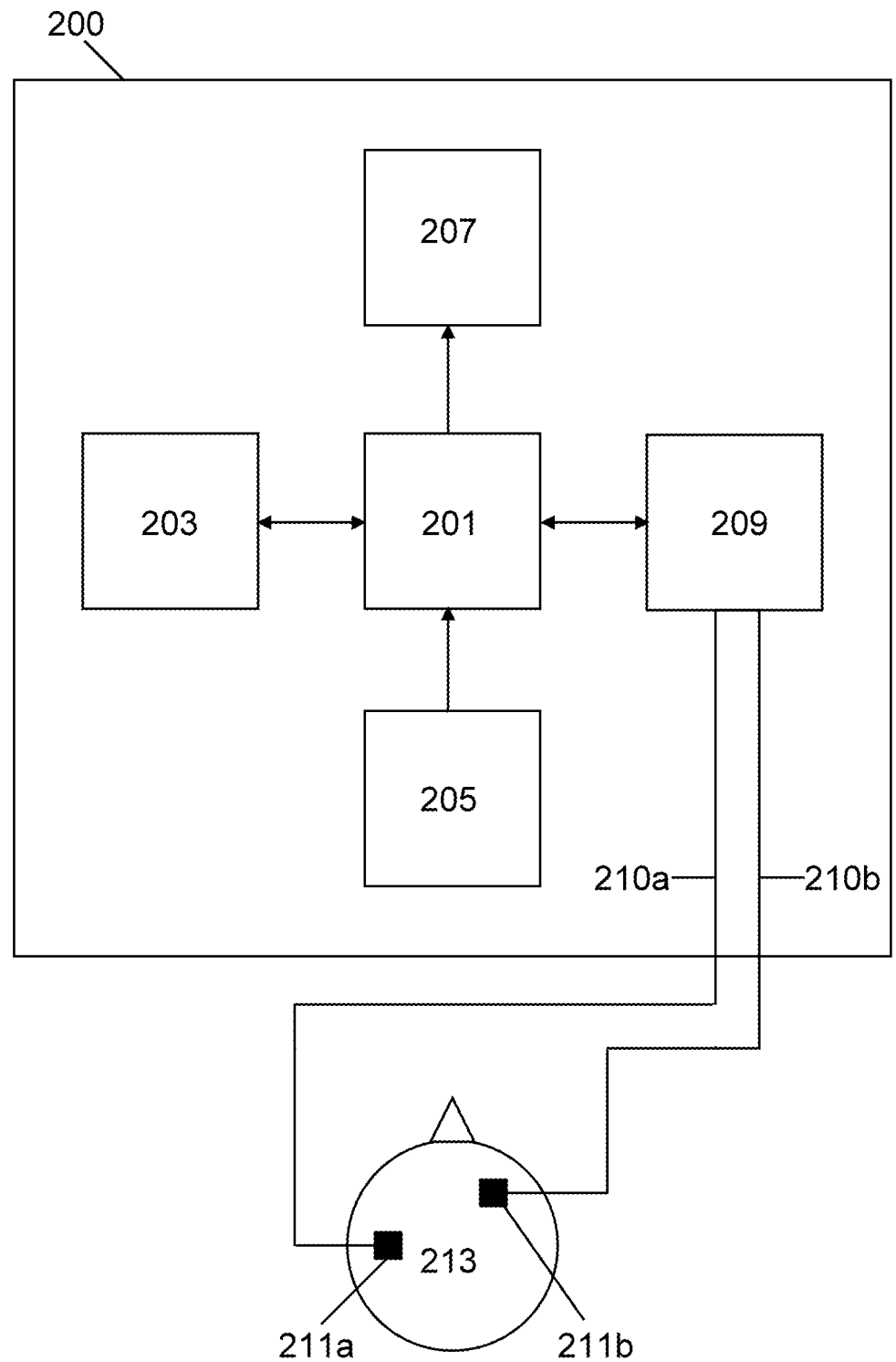
FIG. 26 is a functional block diagram illustrating components of a representative example of a computer and electrical stimulation system for practicing embodiments of the methods of this disclosure.

FIG. 26 schematically illustrates a computer system 200 for, among other things, displaying calculated charge distributions for all or part(s) of the bounding surface of a sulcus where the charge distribution originates, at least in part, from charges on at least part of an electrode for applying current to neural tissue. In this non-limiting, exemplary embodiment, system 200 includes one or more processors 201 and one or more non-transitory, computer-readable storage media 203 (e.g., one or more memories) with data and instructions stored therein that, when used by the one or more processors, perform the step of calculating the charge distribution. Also connected to the one or more processors are one or more input devices 205 for providing inputs to the system, e.g., data and/or control inputs from a user, and one or more displays 207 for providing outputs to a user, e.g., for providing graphical displays of charge distributions to a user.

In embodiments in which current is applied to a subject, the one or more processors can also be connected to one or more current sources 209 which are controlled by and provide feedback to the one or more processors and which through one or more conductors 210*a*,210*b* apply current to a subject through one or more electrodes 211*a*,211*b* which in FIG. 26 are shown as applied to the subject's head 213 for use in, for example, a transcranial DC stimulation procedure. Other electrode locations and stimulation procedures can, of course, be used as desired. Likewise, current can be applied to a subject through a standalone system not integrated with the system used to select electrode locations.

A variety of modifications to the foregoing disclosure will be evident to persons of ordinary skill in the art. The following claims are intended to cover the specific embodiments set forth herein as well as modifications, variations, and equivalents thereof.

What is claimed is:

1. A method for applying electrical current to a neural tissue using at least two electrodes, the neural tissue having at least one sulcus filled with cerebrospinal fluid, the method comprising:
   (a) selecting a location for at least one of the electrodes relative to a location of a sulcus of the neural tissue by calculating, using a computer, a charge distribution for at least a part of the bounding surface of the sulcus, said charge distribution originating at least in part from charges on at least part of the electrode; and
   (b) applying electrical current to the neural tissue using an electrode substantially at the location selected in step (a),
   wherein in step (a), selecting a location for at least one of the electrodes comprises a pixel-as-a-sensor process.

2. The method of claim 1 wherein in step (a), calculating the charge distribution comprises pixelizing the at least a part of the bounding surface of the sulcus and computing charge per pixel values for surface pixels resulting from the pixelization.

3. The method of claim 1 wherein in step (a), the location of the electrode is selected relative to more than one sulcus.

4. The method of claim 1 wherein in step (a), locations are selected for a plurality of electrodes relative to a location of a sulcus.

5. The method of claim 1 wherein in step (a), locations are selected for a plurality of electrodes relative to more than one sulcus.

6. The method of claim 1 wherein in step (a), selecting a location for at least one of the electrodes comprises displaying at least a part of the calculated charge distribution.

7. The method of claim 6 wherein the displaying comprises displaying at least one polarity plot.

8. The method of claim 7 wherein the displaying comprises displaying a time series of polarity plots.

9. The method of claim 6 wherein the displaying comprises displaying at least one trace along at least one part of the bounding surface of the sulcus.

10. The method of claim 6 wherein the displaying comprises displaying a sum of charges on a portion of the bounding surface of the sulcus.

11. The method of claim 1 wherein in step (a), the at least part of the bounding surface of the sulcus comprises at least a part of the mouth of the sulcus.

12. The method of claim 1 wherein in step (a), the at least part of the bounding surface of the sulcus comprises at least a part of an end portion of the bounding surface.

13. The method of claim 1 wherein in step (a), the at least part of the bounding surface of the sulcus comprises at least a part of a side portion of the bounding surface.

14. The method of claim 1 wherein step (b) comprises applying current invasively, non-invasively, or both invasively and non-invasively to brain tissue, spinal cord tissue, peripheral nerve tissue, or combinations thereof.

15. The method of claim 1 wherein step (b) comprises applying DC current, AC current, random noise current, pulsed current, or combinations thereof.

16. A method for applying electrical current to a neural tissue using at least two electrodes, the neural tissue having at least one sulcus filled with cerebrospinal fluid, the method comprising:
   (a) selecting a location for at least one of the electrodes relative to a location of a sulcus of the neural tissue by calculating, using a computer, a charge distribution for at least a part of the bounding surface of the sulcus, said charge distribution originating at least in part from charges on at least part of the electrode; and
   (b) applying electrical current to the neural tissue using an electrode substantially at the location selected in step (a),
   wherein in step (a), calculating the charge distribution comprises pixelizing the at least a part of the bounding surface of the sulcus and modeling each surface pixel resulting from the pixelization as a sensor for charges of other surface pixels and charges of the at least two electrodes.

17. The method of claim 16 wherein modeling each surface pixel as a sensor comprises computing solid angles of said surface pixel as seen from other surface pixels and the at least two electrodes.

* * * * *